(12) United States Patent
Nezami

(10) Patent No.: US 11,369,585 B2
(45) Date of Patent: Jun. 28, 2022

(54) COMPOSITIONS, METHODS, SYSTEMS AND/OR KITS FOR PREVENTING AND/OR TREATING NEOPLASMS

(71) Applicant: Research Cancer Institute of America, Fresno, CA (US)

(72) Inventor: Mohammed Amin Nezami, Clovis, CA (US)

(73) Assignee: RESEARCH CANCER INSTITUTE OF AMERICA, Newport Beach, CA (US)

(*) Notice: Subject to any disclaimer, the term of this patent is extended or adjusted under 35 U.S.C. 154(b) by 150 days.

(21) Appl. No.: 16/494,730

(22) PCT Filed: Mar. 16, 2018

(86) PCT No.: PCT/US2018/022973
§ 371 (c)(1),
(2) Date: Sep. 16, 2019

(87) PCT Pub. No.: WO2018/170457
PCT Pub. Date: Sep. 20, 2018

(65) Prior Publication Data
US 2020/0147030 A1    May 14, 2020

Related U.S. Application Data

(60) Provisional application No. 62/473,230, filed on Mar. 17, 2017.

(51) Int. Cl.
| | |
|---|---|
| *A61K 31/352* | (2006.01) |
| *A61P 35/00* | (2006.01) |
| *A61K 31/166* | (2006.01) |
| *A61K 31/192* | (2006.01) |
| *A61K 31/4184* | (2006.01) |
| *A61K 31/4439* | (2006.01) |
| *A61K 31/496* | (2006.01) |
| *A61K 31/502* | (2006.01) |
| *A61K 31/5025* | (2006.01) |
| *A61K 31/55* | (2006.01) |

(52) U.S. Cl.
CPC .......... *A61K 31/352* (2013.01); *A61K 31/166* (2013.01); *A61K 31/192* (2013.01); *A61K 31/4184* (2013.01); *A61K 31/4439* (2013.01); *A61K 31/496* (2013.01); *A61K 31/502* (2013.01); *A61K 31/5025* (2013.01); *A61K 31/55* (2013.01); *A61P 35/00* (2018.01)

(58) Field of Classification Search
CPC .................................................. A61K 31/352
See application file for complete search history.

(56) References Cited

U.S. PATENT DOCUMENTS

| | | |
|---|---|---|
| 4,569,836 A | 2/1986 | Gordon |
| 6,299,925 B1 | 10/2001 | Xiong et al. |
| 6,376,525 B1 | 4/2002 | Kong |
| 8,933,078 B2 | 1/2015 | Nezami |
| 9,364,500 B2 | 6/2016 | Nezami |
| 9,439,899 B2 | 9/2016 | Proia |
| 10,016,392 B2 | 6/2018 | Nezami |
| 2003/0103954 A1 | 6/2003 | Rosenbloom |
| 2003/0105031 A1 | 6/2003 | Rosenbloom |
| 2006/0035981 A1 | 2/2006 | Mazzio et al. |
| 2006/0057230 A1 | 3/2006 | Chow |
| 2007/0190022 A1 | 8/2007 | Bacopoulos et al. |
| 2007/0190114 A1 | 8/2007 | Smart |
| 2008/0305096 A1 | 12/2008 | Verdegem et al. |
| 2010/0316733 A1 | 12/2010 | Locklear |
| 2010/0330087 A1 | 12/2010 | Newell et al. |
| 2011/0104100 A1 | 5/2011 | Riordan et al. |
| 2011/0118309 A1 | 5/2011 | Atadja |
| 2011/0224290 A1 | 9/2011 | Estrela Ariquel et al. |
| 2012/0121730 A1 | 5/2012 | Singh |
| 2012/0269861 A1 | 10/2012 | Sherman et al. |
| 2013/0011488 A1* | 1/2013 | Nezami ................ A61K 9/0019 424/600 |
| 2013/0129809 A1 | 5/2013 | Srivastava et al. |
| 2015/0366838 A1 | 12/2015 | Lines |
| 2017/0014376 A1 | 1/2017 | Nezami |
| 2017/0020842 A1 | 1/2017 | Elmann |
| 2017/0285027 A1 | 10/2017 | Fantl |
| 2018/0133278 A1 | 5/2018 | Atamaniuk et al. |
| 2019/0125791 A1 | 5/2019 | Wilmotte |

(Continued)

FOREIGN PATENT DOCUMENTS

| | | |
|---|---|---|
| CN | 1537161 | 10/2004 |
| CN | 1965715 | 5/2007 |

(Continued)

OTHER PUBLICATIONS

U.S. Appl. No. 16/488,565, January, Nezami.*
Arney, Coming ever closer—first PARP inhibitor licensed in Europe, Oct. 24, 2014, last edited Dec. 22, 2015, available at https://news.cancerresearchuk.org/2014/10/24/coming-ever-closer-first-parp-inhibitor-on-track-to-be-licensed-in-europe/.*
Azvolinsky, MBCC: PARP Inhibitors for Breast Cancer—Which Subpopulation to Target?, Mar. 16, 2012, available at https://www.cancernetwork.com/view/mbcc-parp-inhibitors-breast-cancerwhich-subpopulation-target.*
Zips et al., In vivo, 2005, 19, 1-8.*
Sikora, Current Science 2001, 81(5), 549-554.*
Schmutzler et al. European Journal of Endocrinology 2000, 143, 15-24.*

(Continued)

*Primary Examiner* — Svetlana M Ivanova
(74) *Attorney, Agent, or Firm* — Knobbe, Martens, Olson & Bear LLP

(57) ABSTRACT

Provided herein are compositions, methods, systems and/or kits for preventing and/or treating neoplasms using at least one of quercetin, sodium phenyl butyrate and epigallocatechin-3-gallate in combination with one or more anti-cancer agents. The compositions, methods, systems and/or kits are used to prevent and/or treat neoplasms that are resistant to the one or more anti-cancer agents when administered alone.

11 Claims, 21 Drawing Sheets

(56) References Cited

U.S. PATENT DOCUMENTS

| | | | |
|---|---|---|---|
| 2019/0167634 | A1 | 6/2019 | Nezami |
| 2020/0206183 | A1 | 7/2020 | Nezami |
| 2021/0015787 | A1 | 1/2021 | Nezami |
| 2021/0283149 | A1 | 9/2021 | Nezami |
| 2021/0401799 | A1 | 12/2021 | Nexami |

FOREIGN PATENT DOCUMENTS

| | | | |
|---|---|---|---|
| EP | 1 847 274 | 10/2007 | |
| JP | 05-070348 | 3/1993 | |
| JP | 2006 298781 | 11/2006 | |
| WO | WO 97/47317 | 12/1997 | |
| WO | WO 05/023179 | 3/2005 | |
| WO | WO 05/083123 | 9/2005 | |
| WO | WO 06/059237 | 6/2006 | |
| WO | WO 07/121088 | 10/2007 | |
| WO | WO 08/011363 | 1/2008 | |
| WO | WO 08/082856 | 7/2008 | |
| WO | WO 09/019721 | 2/2009 | |
| WO | WO 11/112156 | 9/2011 | |
| WO | WO 14/091078 | 6/2014 | |
| WO | WO 14/111268 | 7/2014 | |
| WO | WO-2016054237 A2 * | 4/2016 | ........... C07D 319/06 |
| WO | WO 18/170457 | 9/2018 | |

OTHER PUBLICATIONS

Nagano et al., A prospective study of green tea consumption and cancer incidence, Hiroshima and Nagasaki, Cancer Cases and Control 12: 501-508, 2001.*

Alexandrov et al., Signatures of mutational processes in human cancer, Nature vol. 500, pp. 415-421 (2013), available at https://www.nature.com/articles/nature12477.*

Akbas et al, "The effect of quercetin on topotecan cytotoxicity in MCF-7 and MDA-MB 231 human breast cancer cells." J Surg Res. May 1, 2005;125(1):49-55.

Alleva et al., 2005, α-Lipoic acid supplementation inhibits oxidative damage, accelerating chronic wound healing in patients undergoing hyperbaric oxygen therapy, Biochemical and Biophysical Research Communications, 333:404-410.

American Cancer Society, Quercetin, 4 pp., no date.

Amirkhosravi et al., "Pentoxifylline inhibits hypoxia-induced upregulation of tumor cell tissue factor and vascular endothelial growth factor." ThrombHaemost. Oct. 1998;80(4):598-602.

Arce et al., 2006, A proof-of-principle study of epigenetic therapy added to neoadjuvant doxorubiin cyclophosphamide for locally advanced breast cancer, PLoS One, 2006, 1(1):e98.

Armeanu et al., "Natural killer cell-mediated lysis of hepatoma cells via specific induction of NKG2D ligands by the histone deacetylase inhibitor sodium valproate" Can Res Jul. 15, 2005 vol. 65 No. 14 pp. 6321-6329.

Bai et al., Jan. 2010, Myricetin and quercetin are naturally-occuring co-substrates of cyclooxygenases in vivo, Prostaglandins Leukot Essent Fatty Acids, 82(1):1-11.

Baker et al., "A practical assay of lipoate in biologic fluids and liver in health and disease." Free Radic Biol Med. Sep. 1998; 25(4-5):473-479.

Befon et al., "Continuous Subcutaneous Octreotide in Gastrointestinal Cancer Patients: Pain Control and B-Endorphin Levels", Anticancer Research, 20:4039-4046 (2000) (abstract).

Bettuzzi et al., "Chemoprevention of human prostate cancer by oral administration of green tea catechins in volunteers with high-grade prostate intraepithelial neoplasia: a preliminary report from a one-year proof-of principle study," Cancer Res, Jan. 15, 2006, 66:1234-1240.

Bonnet et al., "A mitochondria-K+ channel axis is suppressed in cancer and its normalization promotes apoptosis and inhibits cancer growth." Cancer Cell. Jan. 2007;11(1):37-51.

Boyd, "Insulin and cancer." Integr Cancer Ther. Dec. 2003, 2(4):315-29.

Cai et al., "Restorative effect of quercetin on subcellular distribution of daunorubicin in multidrug resistant leukemia cell lines K562/ADM and HL-60/ADM." Department of Oncology, Shanghai No. 6 People's Hospital, Shanghai Jiaotong University, Shanghai 200233, P.R. China, Ai Zheng. Dec. 2004;23(12):1611-1615 (abstract).

Cairns et al., "Metabolic targeting of hypoxia and HIF1 in solid tumors can enhance cytotoxic chemotherapy." Proc Natl Acad Sci USA 104: 9445-9450.

Camacho et al., "Phase I dose escalation clinical trial of phenylbutyrate sodium administered twice daily to patients with advanced solid tumors." Invest New Drugs. Apr. 2007;25(2):131-8.

Cao et al., "Dichloroacetate (DCA) sensitizes both wild-type and over expressing Bcl-2 prostate cancer cells in vitro to radiation." Prostate 68: 1223-1231.

Carducci et al., "Phenylbutyrate induces apoptosis in human prostate cancer and is more potent than phenylacetate." Clin Cancer Res. Feb. 1996;2(2):379-87.

Castillo et al., "The effects of the bioflavonoid quercetin on squamous cell carcinoma of the head and neck origin," Am J Surg. 1989;158(4):351-5.

Chang et al., 2006, Reactive oxygen species production is involved in quercetin-induced apoptosis in human helatoma cells, Nutr Cancer, 55(2):201-209 (abstract).

Chen et al., "Quercetin and trichostatin A cooperatively kill human leukemia cells", Pharmazie 60:856-860 (2005).

Chen, L. et al., "Absorption, distribution, elimination of tea polyphenols in rats," Drug Metab Dispos, Sep. 1997, 25(9):1045-1050.

Choi et al., "Mechanism of alpha-lipoic acid-induced apoptosis of luna cancer cells." Ann N Y Acad Sci. Aug. 2009;1171:149-55.

Cruz-Correa et al., Aug. 2006, Combination treatment with curcumin and quercetin of adenomas in familial adenomatous polyposis, Clinical Gastroenterology and Hepatology, 4(8):1035-1038.

Daruwalla et al., "Hyperbaric Oxygen Therapy for Malignancy, A review" World Journal of Surgery, Nov. 2006.

Dashwood et al., "Dietary histone deacetylase inhibitors: From cells to mice to man" Semin Cancer Biol. Oct. 2007, 17(5):363-369.

Dell'Antone, "Inactivation of H+-vacuolar ATPase by the energy blocker 3-bromopyruvate, a new antitumour agent" Life Sci. Oct. 19, 2006;79(21):2049-55.

Dreher et al., "Role of oxygen free radicals in cancer development." Eur J Cancer. Jan. 1996;32A(1):30-38.

Du et al., "Dietary quercetin combining intratumoral doxorubicin injection synergistically induces rejection of established breast cancer in mice." Int Immunopharmacol. Jul. 2010;10(7):819-26.

Du et al., "Quercetin greatly improved therapeutic index of doxorubicin against 4T1 breast cancer by its opposing effects on HIF-1.alpha. in tumor and normal cells." Cancer Chemother Pharmacol. Jan. 2010;65(2):277-87.

Fang et al.,"Dietary Polyphenols May Affect DNA Methylation", J. Nutr., Jan. 2007, vol. 137.

Farr, Charles, "The Therapeutic Use of Intravenous Hydrogen Peroxide", A Review, Experimental Evidence of Physiological Effect and Clinical Experience, Nov. 1986, 11 pp.

Ferry et al., "Phase I clinical trial of the flavonoid quercetin: pharmacokinetics and evidence for in vivo tyrosine kinase inhibition." Clin Cancer Res. Apr. 1996;2(4):659-68.

Ganapathy-Kanniappan et al., "3-Bromopyruvate induces endoplasmic reticulum stress, overcomes autophagy and causes apoptosis in human HCC cell lines." Anticancer Res. Mar. 2010;30(3):923-35.

Ganapathy-Kanniappan et al., "3-bromopyruvate: a new targeted antiglycolytic agent and a promise for cancer therapy." Curr Pharm Biotechnol. Aug. 2010;11(5):510-517.

Garcia-Roman et al, "VEGF secretion during hypoxia depends on free radicals-induced Fyn kinase activity in mast cells." BiochemBiophys Res Commun. Oct. 15, 2010;401(2):262-7.

Gilbert et al., "A phase I dose escalation and bioavailability study of oral sodium phenylbutyrate in patients with refractory solid tumor malignancies." Clinical Cancer Research Aug. 2001, 7:2292-2300.

Glaser KB, "HDAC inhibitors: Clinical update and mechanism-based potential", Biochem Pharmacol (2007).

(56) References Cited

OTHER PUBLICATIONS

Gore et al., Apr. 2002, Impact of prolonged infustions of the putative differentiating agent sodium phenylbutyrate on myelodysplastic syndromes and acute myeloid leukemia, Clinical Cancer Resarch, 8:963-970.
Gore, Steven D. et al., "Combined DNA Methyltransferase and Histone Deacetylase Inhibition in the Treatment of Myeloid Neoplasms," Cancer Res 2006; 66:6361-6369.
Gorospe et al., "Up-regulation and functional role of p21Waf1/Cip1 during growth arrest of human breast carcinoma MCF-7 cells by phenylacetate." Cell Growth Differ. Dec. 1996;7(12):1609-15.
Granowitz et al., "Hyperbaric Oxygen Inhibits benign and malignant human mammary epithelial cell proliferation" Anticancer Res. Nov.-Dec. 2005;25(6B):3833-42.
Grimberg et al., "Role of insulin-like growth factors and their binding proteins in growth control and carcinogenesis." J Cell Physiol. Apr. 2000;183(1):1-9.
Guevara-Aguirre et al., "Growth hormone receptor deficiency is associated with a major reduction in pro-aging signalling, cancer, and diabetes in humans." Sci Transl Med. Feb. 16, 2011;3(70):70ra13.
Han et al., "Effect of glycolytic inhibitors on proliferation and apoptosis of pancreatic cancer cell under hypoxic condition", Chinese Journal of General Surgery, Mar. 2009, 18(3):243-246.
Han, S. et al., "Differentiation of human neuroblatoma by phenylacetate is mediated by peroxisome proliferator-activated receptor gamma," Cancer Res., May 15, 2001, vol. 61:3998-4002.
Haroon et al., "Lung metastic load limitation with hyperbaric oxygen," Undersee Hyperb Med., Mar.-Apr. 2007, 34(2):83-90.
Hashemzae et al., Aug. 2017, Anticancer and apoptosis-inducing effects of quercetin in vitro and in vivo, Oncology Reports, 38(2):819-828.
Hastak, K. et al., "Role of p53 and NF-kappaB in epigallocatechin-3-gallate-induced apoptosis of LNCaP cells," Oncogene, Jul. 31, 2003, 22:4851-4859.
Hong, J. et al., "Stability, cellular update, biotransformation, and efflux of tea polyphenol (−)-epigallocatechin-3-gallate in HT-29 human colon adenocarcinoma cells," Cancer Res Dec. 15, 2002, 62:7251-7246.
Hsu et al., "Chemoresistance of lung cancer stemlike cells depends on activation of Hsp27," Cancer. Apr. 1, 2011;117(7):1516-28.
Iannitti et al., 2011, Clinical and experimental applications of sodium phenylbutyrate, Drugs, 11(3):227-249.
Ishikawa, A. et al., "Smoking, alcohol drinking, green tea consumption and the risk of esophageal cancer in Japanese men," J Epidemiol, Sep. 2006, 16(5):185-192.
Israel, M. et al., "The metabolic advantage of tumor cells," Mol Cancer, Jun. 7, 2011, 10:70.
Jia et al., "Histone hyperacetylation is involved in the quercetin-induced human leukemia cell death", Pharmazie, 2008, 63:379-383.
Jian, L. et al., "Protective effect of green tea against prostate cancer: a case-control study in southeast China," Int J Cancer, Jan. 1, 2004, 108:130-135.
Jung et al., "EGCG, a major component of green tea, inhibits tumour growth by inhibiting VEGF induction in human colon carcinoma cells," Br J Cancer, Mar. 23, 2001, vol. 84.
Jung et al., "Inhibition of tumour invasion and angiogenesis by epigallocatechin gallate (EGCG), a major component of green tea," Int J Exp Pathol, Dec. 2001, 82:309-316.
Kanadaswami et al., "The antitumor activities of flavonoids." In Vivo. Sep.-Oct. 2005;19(5):895-909.
Kaplan et al., "The Insulin-like Growth Factor Axis and Prostate Cancer: Lessons from the Transgenic Adenocarcinoma of Mouse Prostate (TRAMP) Model 1" Cancer Res May 5, 1999 59; 2203.
Kawada et al., "Insulin-like Growth Factor I Secreted from Prostate Stromal Cells Mediates Tumor-Stromal Cell Interactions of Prostate Cancer" Cancer Res Apr. 15, 2006 66:4419-4425.
Khan et al., "Cancer Chemoprevention Through Dietary Antioxidants: Progress and Promise", Antioxidants and Redox Signaling, vol. 10, No. 3, pp. 475-510, 2008.
Kim et al., "Inhibition of vascular endothelial growth factor induced angiogenesis suppresses tumour growth in vivo" Nature, Apr. 29, 1993, 362:841-844.
Ko et al., "Advanced cancers: eradication in all cases using 3-bromopyruvate therapy to deplete Atp." BiochemBiophys Res Commun. Nov. 5, 2004;324(1):269-275.
Ko et al., "Glucose catabolism in the rabbit VX2 tumor model for liver cancer: characterization and targeting hexokinase," Cancer Lett. Nov. 8, 2001;173(1):83-91.
Koshikawa et al., "Reactive oxygen species generating mitochondrial DNA mutation up regulates hypoxia inducible factor-1 alpha gene transcription via phosphatidylinositol 3-kinase-Akt/protein kinase C/ histone deacetylase pathway" J Biol Chem. Nov. 27, 2009, 284(48):33185-94.
Kurahashi, N. et al., "Green tea consumption and prostate cancer risk in Japanese men: a prospective study," Am J Epidemiol, Jan. 1, 2008, 167(1):71-77.
Kurmasheva et al., "The insulin-like growth factor-1 receptor-targeting antibody, CP-751,871, suppresses tumor-derived VEGF and synergizes with rapamycin in models of childhood sarcoma." Cancer Res. Oct. 1, 2009;69(19):7662-71.
Kurzrock et al., Mar. 7, 2008, Targeted Cancer Therapy, Springer Science & Business Media, p. 362.
Lamson et al., "Antioxidants and Cancer III: Quercetin", Alternative Medicine Review, 5(3):196-208, 2000.
Lee et al., "Role of Bax in quercetin-induced apoptosis in human prostate cancer cells," Biochem Pharmacol. Jun. 15, 2008;75(12):2345-55.
Leroith et al., "The insulin-like growth factor system and cancer." Cancer Lett. Jun. 10, 2003:195(2):127-37.
Levy, J et al., "Tyrosine protein kinase activity in the DMBA-induced rat mammary tumor: inhibition by quercetin," Biochem Biophys Res Commun., Sep. 28, 1984, 123(3):1227-1233.
Li et al., "Synergistic epigenetic reactivation of estrogen receptor-.alpha. (ER.alpha.) by combined green tea polyphenol and histone deacetylase inhibitor in ER.alpha.-negative breast cancer cells", Molecular Cancer, Biomed Central, Oct. 14, 2010, 9(1):274.
Lin et al., Oct. 1, 2009, A phase I dose-finding study of 5-azacytidine in combination with sodium phenylbutyrate in patients with refractory solid tumors, Clin Cancer Res, 15(19):6241-6249.
Liu et al., "Transcriptional upregulation of TGF-alpha by phenylacetate and phenylbutyrate is associated with differentiation of human melanoma cells." Cytokine. Jul. 1995;7(5):449-56.
Major et al., "The Role of Octreotide in the Management of Patients with Cancer", Ontario Cancer Center, Practice Guideline Report 12-7, Aug. 2004, 37 pp.
Maki, "Small is beautiful: insulin-like growth factors and their role in growth, development, and cancer." J Clin Oncol. Nov. 20, 2010;28(33):4985-95. Epub Oct. 25, 2010.
Martinet et al., "Interpreting clinical assays for histone deacetylase inhibitors." Cancer Manag Res. 2011; 3: 117-141.
Mathupala et al., "Hexokinase II: cancer's double-edged sword acting as both facilitator and gatekeeper of malignancy when bound to mitochondria." Oncogene. Aug. 7, 2006;25(34):4777-86.
Mehrabian, S., "The study of antioxidant and anticarcinogenic green tea and black tea," Pak J Biol Sci, Mar. 15, 2007, 10(6):989-991.
Meng, Studies on the differentiation of human hepatocarcinoma cell induced by historne deacetylase inhibitors and its mechanism, China Doctoral Dissertaions Full-Test Database, p. E-072-39.
Michelakis, E.D. et al., "Metabolic Modulation of Glioblastoma with Dichloroacetate," Science Translational Medicine, Mar. 12, 2010, 2(31):989-994.
Michelakis, et al., "Dichioroacetate (DCA) as a potential metabolic-targeting therapy for cancer." Br J Cancer. Oct. 7, 2008;99(7):989-94.
Millauer et al., "Glioblastoma growth inhibited in vivo by a dominant-negative Flk-1 mutant." Feb. 10, 1994, Nature, 367:576-579.
Mokrzycki "Anti-atherosclerotic efficacy of quercetin and sodium phenylbutyrate in rabbits", Ann Acad Med Stetin, 2000; 46:189-200 (abstract).
Molnar et al., "Antitumor activity of flavonoids on NK/Ly ascites tumor cells." Neoplasma. 1981;28(1):11-18.

(56) References Cited

OTHER PUBLICATIONS

Monneret et al., "Histone deacetylase inhibitors", European Journal of Medicinal Chemistry, Jan. 2005, 40(1):1-13.
Moussa et al., "Hyperbaric oxygen as an adjuvant to cisplatin containing regimen: a companion to a hard journey" Proc Am Soc Clin Oncol 21: 2002 (abstr 2806).
Mukhtar, H. et al., "Tea polyphenols: prevention of cancer and optimizing health," Am J Clin Nutr, Jun. 2000, vol. 71.
Mulholland et al., "Pre-clinical and clinical study of QC12, a water-soluble, pro-drug of quercetin," Annals Oncol Feb. 2001 vol. 12 No. 2 pp. 245-248.
Murray, Quercetin, in How to Prevent and Treat Cancer with Natural Medicine Penguin, Nov. 4, 2003, Health and Fitness, 5 pp.
Mydio et al., "Prostate Cancer: Science and Clinical Practice (Google eBook)", Academic Press, p. 523, Jul. 11, 2003.
Nagano, J. et al., "A prospective study of green tea consumption and cancer incidence, Hiroshima and Nagasaki (Japan),"—Cancer Causes Control, Aug. 2001, 12:501-508.
Nam, S. et al., "Ester bond-containing tea polyphenols potently inhibit proteasome activity in vitro and in vivo," J Biol Chern, Apr. 20, 2001, 276:13322-13330.
Navarro-Peran et al., "The antifolate activity of tea catechins," Cancer Res, Mar. 15, 2005, 65:2059-2064.
Niedzwiecki et al., Sep. 9, 2016, Anticancer efficacy of polyphenols and their combinations, Nutrients, 8(9):1-17.
Nihal et al., "Anti-melanoma effects of vorinostat in combination with polyphenolic antioxidant Epigallocatechin-3-Gallate (EGCG)", Pharmaceutical Research, 27(6):1103-1114, Jun. 2010.
Pedersen PL, "Transport ATPases into the year 2008: a brief overview related to types, structures, functions and roles in health and disease." J Bioenerg Biomembr. Dec. 2007;39(5-6):349-355.
Pedersen, PL, "The cancer cell's "power plants" as promising therapeutic targets: an overview." J Bioenerg Biomembr. Feb. 2007;39(1):1-12.
Pelicano et al., 2008, Glycolysis inhibition for anticancer treatment, Oncogene, 25:4633-4646.
Phuphanich et al., "Oral sodium phenylbutyrate in patients with recurrent malignant gliomas: a dose escalation and pharmacologic study." Neuro Oncol 2005; 7(2):177-182.
Pisters, KM et al., "Phase I trial of oral green tea extract in adult patients with solid tumors," J Clin Oncol, Mar. 15, 2001, 19(6):1830-1838.
Plate et al., "Vascular endothelial growth factor is a potent tumour angiogenesis factor in human gliomas in vivo." Oct. 29, 1992, Nature, 359:845-848.
Pollak et al., "Insulin, insulin-like growth factors, insulin resistance, and neoplasia[1-4]" Am J Clin Nutr. Sep. 2007;86(3):s820-2.
Pollak, "Insulin and insulin-like growth factor signalling in neoplasia." Nat Rev Cancer. Dec. 2008;8(12):915-928.
Pollak, Michael N. et al., "Insulin-like Growth Factors and Neoplasia," Nature Reviews: Cancer, Jul. 2004, 4:505-518.
Prophylaxis, dictionary definition, retrieved on Jun. 25, 2014 from: Vocabulary.com, 4 pp.
Prostate Cancer, Medline Plus, downloaded at http://www.nlm.nih.gov/medlineplus/print/ency/article/000380.htm, Nov. 9, 2009.
Qian et al., "Targeting tumor angiogenesis with histone deacetylase inhibitors: the hydroxamic acid derivative LBH589." Clin Cancer Res. Jan. 15, 2006;12(2):634-42.
Rokes et al., "Sorafenib Plus Valproic Acid for Infant Spinal Glioblastoma," J Pediatr Hematol Concol, Aug. 2010, 32:511-514.
Roomi, MW. et al., "In vivo antitumor effect of ascorbic acid, lysine, proline and green tea extract on human prostate cancer PC-3 xenografts in nude mice: evaluation of tumor growth and immunohistochemistry," In Vivo, Jan.-Feb. 2005, 19:179-184.
Sasabe et al., "Mechanism of HIF-1alpha-dependent suppression of hypoxia-induced apoptosis in squamous cell carcinoma cells." Cancer Sci. Jul. 2005;96(7):394-402.
Scatena et al., "Glycolytic enzyme inhibitors in cancer treatment", Expert Opinion on Investigational Drugs, Informa Healthcare, 17(10):1533-1545, Oct. 2008.

Schwartz et al., "A combination of alpha lipoic acid and calcium hydroxycitrate is efficient against mouse cancer models: preliminary results." Oncol Rep. May 2010;23(5):1407-16.
Selvendiran, "Oxygnation inhibits ovarian tumor growth by downregulating STATS and cyclin-D1 expression" Cancer biol Ther, Aug. 2010, 10(4):386-390.
Shabbeer et al., "Focus on Deacetylation for Therapeutic Benefit", Idrugs, Current Drugs Ltd, Feb. 2005, 8(2):144-154.
Shanafelt, Tait D. et al., "Phase I Trial of Daily Oral Polyphenon E in Patients with Asymptomatic Rai Stage 0 to II Chronic Lymphocytic Leukemia," Journal of Clinical Oncology, Aug. 10, 2009, 27(23):3808-3814.
Shankar, S. et al., "EGCG inhibits growth, invasion, angiogenesis and metastasis of pancreatic cancer," Front Biosci, Jan. 1, 2008, 13:440-452.
Sharma et al., "Molecular pathways in the chemosensitization of cisplatin by quercetin in human head and neck," Cancer BiolTher (2005) 4(9): 949-55.
Shoskes et al., "Quercetin in Men with Category III Chronic Prostatitis: A Preliminary Prospective, Double-Blind, Placebo-Controlled Trial", Urology 54 (6), pp. 960-963, 1999.
Shweiki et al., "Vascular endothelial growth factor induced by hypoxia may mediate hypoxia-initiated angiogenesis." Oct. 29, 1992, Nature, 359:843-845.
Staedler et al., "Drug combinations with quercetin: doxorubicin plus quercetin in human breast cancer cells." Cancer Chemother Pharmacol. Nov. 2011;68(5):1161-1172.
Sun, CL. et al., "Green tea, black tea and breast cancer risk: a meta-analysis of epidemiological studies," Carcinogenesis, Jul. 2006, 27(7):1301-1309.
Sung et al., "Combination of cytotoxic-differentiation therapy with 5-fluorouracil and phenylbutyrate in patients with advanced colorectal cancer." Anticancer Res. Mar.-Apr. 2007;27(2):995-1001.
Suzuki, Y. et al., "Green tea and the risk of breast cancer: pooled analysis of two prospective studies in Japan," Br J Cancer, Apr. 5, 2004, 90:1361-1363.
Takenouchi et al., "Studies on the metabolism of thioctic acid in skin diseases 2. Loading test of thioctic acid in various skin diseases" The Journal of Vitaminology 8, 99-114 (1962).
Tang et al., "The dietary bioflavonoid quercetin synergizes with epigallocathechin gallate (EGCG) to inhibit prostate cancer stem cell characteristics, invasion, migration and epithelial-mesenchymal transition." J Mol Signal. Aug. 18, 2010;5:14.
Tosetti, F., "Angioprevention: angiogenesis is a common and key target for cancer chemopreventive agents," FASEB, J Jan. 2002, vol. 16, 14 pp.
Troy et al., Remington: The Science and Practice of Pharmacy, p. 838, 2006.
Vaupel, "The Role of Hypoxia-Induced Factors in Tumor Progression" Oncologist. 2004;9 Suppl 5:10-17.
Wada et al., "A study on the metabolism of lipoic acid and lipoamide" The Journal of Vitaminology 7, 237-242 (1960).
Wang et al., "Co-treatment with quercetin to enhance the chemopreventive effect of green tea in prostate cancer", FASEB J., Apr. 2010, Meeting Abstract Supplement. Abstract.
Wang et al., Mar. 27, 2012, Quercetin increased the antiproliferative activity of green tea polyphenol (−)-epigallocatechin gallata in prostate cancer cells, Nutrition and Cancer, 64(4):580-587.
Wang, Studies on the apoptosis of NB4 cells induced by hsitone deacetylase inhibitors in combination with ATRA and As2O3 and its mechanism, China Master's Dissertations Full-Test Database, p. 3072-35.
Wardell et al., "Glucose metabolism as a target of histone deacetylase inhibitors." Mol Endocrinol. Mar. 2009;23(3):388-401.
Wenzel et al., "Alpha-Lipoic acid induces apoptosis in human colon cancer cells by increasing mitochondrial respiration with a concomitant O2-*-generation" Apoptosis. Mar. 2005;10(2):359-368.
Wong et al., "Dichloroacetate induces apoptosis in endometrial cancer cells" Gynecol Oncol 109: 394-402.
Wu, AH et al., "Green tea and risk of breast cancer in Asian Americans," Int J cancer. Sep. 10, 2003, 106:574-579.

(56) References Cited

OTHER PUBLICATIONS

Yang et al., "Cancer prevention by tea: animal studies, molecular mechanisms and human relevance," Nat Rev Cancer, Jun. 2009, 9:429-439.
Yang, CS., et al, "Inhibition of carcinogenesis by tea," Annu RevPharmacol Toxicol, 2002, 42:25-54.
Yang, Gong et al., "Prospective Cohort Study of Green Tea Consumption and Colorectal Cancer Risk in Women," Cancer Epidemiol Biomarkers Prev, Jun. 2007, 16:1219-1223.
Yoon, Joo-Heon et al., "Molecular Targets of Dietary Polyphenols with Anti-inflammatory Properties," Yonsei Med J., Oct. 31, 2005, 46(5):585-596.
Zhang et al., "Sodium 4-phenylbutyrate induces apoptosis of human lung carcinoma cells through activating JNK pathway." J Cell Biochem. Nov. 1, 2004;93(4):819-29.
Zhou et al., "Dietary polyphenol quercetin targets pancreatic cancer stem cells." Int J Oncol. Sep. 2010;37(3):551-561.
International Search Report & Written Opinion, dated May 31, 2018, in International Patent Application No. PCT/US2018/022973.
American Cancer Society, 2019, How chemotherapy drugs work, https://www.cancer.org/content/dam/CRC/PDF/Public/8418.00.pdf, 9 pp.
Patnaik et al., Jun. 2019, Drugs targeting epigenetic modifications and plausible therapeutic strategies against colorectal cancer, Frontiers in Pharmacology, 10(588), 15 pp.
Taylor, 2017, Synergism of quercetin and sodium butyrate for controlling growth of glioblastoma, Master's thesis, University of South Carolina, retrieved from https://scholarcommons.sc.edu.etd.4149, 102 pp.
Xintaropoulou et al., 2008, A comparative analysis of inhibitors of the glycolysis pathway in breast and ovarian cancer cell line models, Onotarget, 6(27):25677-25695.
Ciesielski et al., 2020, Epigallocatechin-3-gallate (EGCG) alters histone acetylation and methylation and impacts chromatin architecture profile in human endothelial cells, Molecules, 25:2326.
Harris et al., Oct. 2016, Quercetin as an emerging anti-melanoma agent: a four-focus area therapeutic development strategy, Frontiers in Nutrition, 5(48), 14 pp.
Ansel et al., 1999, Drug dosage and terminology, in Pharmacetuical Dosage Forms and Drug Delivery Systems, 7th Ed., Lippincott Williams & Wilkins, p. 48.
Cheng et al., Aug. 31, 1989, The study of green tea extract's anti-tumor effect and mechanism of TPA, Zhonggu Kuangzhan Institute of Technology, 11(4):259-264.
Xiao et al., Dec. 31, 1993, University Health Guide, Wubian Dayan Publishing House, 216-217.
Xu et al., Mar. 16, 2015, Enhancing the anti-colon cancer activity of quercetin by self-assembled micelles, International Journal of Nanomedicine, 10:2051-2063.
Zhang , Nov. 15, 2009, Inhibition of glycolysis to the biologic characteristics of pancreatic cancer cell PANC-1 and it mechanism, Kyangyao Health Science and Technoloyg Appraisal, p. 10.
Zheng et al., Feb. 28, 2010, Clinical Biochemical Tests, Zhonggukuang Pharmaceutical Technology Press, pp. 88-90.
Zhou et al., Dec. 31, 1992, Cancer change, abnormal change and sudden change, Research on Cancer Suppressor, 4(2):35-40.

\* cited by examiner

COMPOSITIONS, METHODS, SYSTEMS AND/OR KITS FOR PREVENTING AND/OR TREATING NEOPLASMS

PRIORITY AND CROSS REFERENCE TO RELATED APPLICATIONS

This application is the U.S. National Phase Application under 35 U.S.C. § 371 of International Application No. PCT/US2018/022973, filed Mar. 16, 2018, designating the U.S. and published in English as WO 2018/170457 A1 on Sep. 20, 2018, which claims the benefit of U.S. Provisional Application No. 62/473,230, filed on Mar. 17, 2017, which is hereby incorporated by reference in its entirety.

BACKGROUND

Field

The present disclosure is generally related to compositions, methods, systems and/or kits comprising, consisting of, or consisting essentially of, one or more anti-cancer response modulators in combination with one or more anti-cancer agents for preventing and/or treating neoplasms.

Certain embodiments of the present disclosure are related to compositions, methods, systems and/or kits comprising, consisting of, or consisting essentially of, one or more anti-cancer response modulators in combination with one or more anti-cancer agents for preventing and/or treating neoplasms that are resistant to the one or more anti-cancer agents.

Description of the Related Art

In 2007, the ten most commonly diagnosed cancers among men in the United States included cancers of the prostate, lung, colon, rectum, and bladder; melanomas of the skin; non-Hodgkin's lymphoma; kidney cancer, mouth and throat cancer, leukemia, and pancreatic cancer. In women, the most common cancers were reported as breast, lung and colon cancer. Overall, 758,587 men were told they had cancer and 292,853 men died from cancer in the U.S. in 2007.

In women, there has been a prevalence of 6,451,737 advanced cases reported in 2008 by the Surveillance, Epidemiology, and End Results (SEER) Program of the National Cancer Institute. In general there were 11,957,599 advanced cancer cases in the US reported in 2010 by the Centers for Disease Control and Prevention (CDC) and the incidence has been almost unchanged over the previous 8 years (482,000 cases in 2000 versus 456,000 cases in 2008). There has been an annual change of only approximately 0.6% in cancer incidence between the years of 1999 to 2008.

Triple negative breast cancers i.e., a breast cancer that is estrogen receptor-negative, progesterone receptor-negative and human epidermal growth factor receptor 2 (HER2/NEU)-negative, compromise about 15% of breast cancers overall, about 70% of breast cancers in individuals harboring a germline BRCA1 mutation, and 20% in BRCA2 mutation carriers. Reciprocally, the presence of germ line and/or somatic mutations in BRCA has been widely recognized in triple negative breast cancer.

SUMMARY

In some embodiments, a pharmaceutical composition for prophylaxis, treatment or both of a neoplasm is provided comprising, consisting of, or consisting essentially of, at least one anti-cancer agent, and a first anti-cancer response modulator, wherein the first anti-cancer response modulator is selected form the group consisting of quercetin, sodium phenyl butyrate (SPB) and epigallocatechin-3-gallate (EGCG). In some embodiments, the pharmaceutical composition further comprises, consists of, or consists essentially of, a second anti-cancer response modulator selected form the group consisting of quercetin, SPB and EGCG. In some embodiments, the pharmaceutical composition further comprises, consists of, or consists essentially of, a third anti-cancer response modulator selected form the group consisting of quercetin, SPB and EGCG. In some embodiments of the pharmaceutical composition, the first anti-cancer response modulator is quercetin. In some embodiments of the pharmaceutical composition, the first anti-cancer response modulator is SPB. In some embodiments of the pharmaceutical composition, the first anti-cancer response modulator is EGCG. In some embodiments of the pharmaceutical composition, the second anti-cancer response modulator is quercetin. In some embodiments of the pharmaceutical composition, the second anti-cancer response modulator is SPB. In some embodiments of the pharmaceutical composition, the second anti-cancer response modulator is EGCG. In some embodiments of the pharmaceutical composition, the first, second and third anti-cancer response modulators are quercetin, SPB and EGCG. In some embodiments of the pharmaceutical composition, the at least one anti-cancer agent is poly ADP ribose polymerase (PARP) inhibitor. In some embodiments of the pharmaceutical composition, at least a portion of the pharmaceutical composition is formulated for IV administration or oral administration.

In some embodiments of the pharmaceutical composition, the amount of PARP inhibitor is about 0.5 mg to about 1200 mg per day. In some embodiments of the pharmaceutical composition, the amount of quercetin is 0.1 g to 2.5 g. In some embodiments of the pharmaceutical composition, the quercetin is in solution at a concentration of 10 mg/ml to 500 mg/ml. In some embodiments of the pharmaceutical composition, the amount of SPB is 0.1 g to 40 g. In some embodiments of the pharmaceutical composition, the SPB is in solution at a concentration of 50 mg/ml to 500 mg/ml. In some embodiments of the pharmaceutical composition, the amount of EGCG is 0.1 g to 1.5 g. In some embodiments of the pharmaceutical composition, the EGCG is in solution at a concentration of 5 mg/ml to 50 mg/ml.

In some embodiments of the pharmaceutical composition, the anti-cancer agent and at least one anti-cancer response modulator are in a single dosage form for co-administration. In some embodiments of the pharmaceutical composition, the anti-cancer agent and at least one anti-cancer response modulator are in a single dosage form suitable for IV administration. In some embodiments of the pharmaceutical composition, the anti-cancer agent and at least one anti-cancer response modulator are in a single dosage form suitable for oral administration. In some embodiments of the pharmaceutical composition, the anti-cancer agent and at least one anti-cancer response modulator are in a separate dosage forms. In some embodiments of the pharmaceutical composition, the anti-cancer agent and at least one anti-cancer response modulator are each in dosage forms suitable for IV administration. In some embodiments of the pharmaceutical composition, the anti-cancer agent and at least one anti-cancer response modulator are each in dosage forms suitable for oral administration. In some embodiments of the pharmaceutical composition, either the anti-cancer agent or the at least one anti-cancer response modulator is in a dosage form suitable for oral administration and the other is in a dosage form for IV administration.

In some embodiments, the neoplasm is one or more of breast adenocarcinoma, pancreatic adenocarcinoma, lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, and breast cancer.

In some embodiments, the neoplasm is one or more of breast adenocarcinoma, pancreatic adenocarcinoma, lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, breast cancer, astrocytomas, pilocytic astrocytoma, diffuse astrocytoma, anaplastic astrocytoma, and brain stem gliomas, glioblastomas, glioblastoma multiforme, meningioma, gliomas, ependymomas, oligodendrogliomas, and mixed gliomas, brain tumors, pituitary tumors, craniopharyngiomas, germ cell tumors, pineal region tumors, medulloblastomas, and primary CNS lymphomas.

In some embodiments, a kit for prophylaxis, treatment or both of a neoplasm is provided wherein the kit comprises, consists of, or consists essentially of, a pharmaceutical composition as disclosed herein, wherein the pharmaceutical composition is in a single container. In some embodiments of the kit, each of the at least one anti-cancer agent and the one or more modulators are contained in a single container in a single dosage form. In some embodiments of the kit, each of the at least one anti-cancer agent and the one or more modulators are contained in separate sub-containers.

In some embodiments, use of any of the pharmaceutical compositions or kits disclosed herein for treatment, prevention or both of a neoplasm in a subject in need thereof is provided. In some embodiments, the neoplasm is likely to develop resistance, develops resistance, and/or is already resistant to the at least one anti-cancer agent. In some embodiments, the neoplasm is likely to develop resistance, develops resistance, and/or is already resistant to the one or more modulators.

In some embodiments, a method of prevention, treatment or both of a neoplasm is provided comprising, consisting of, or consisting essentially of, administering any of the compositions disclosed herein to a patient in need thereof. In some embodiments of the method, the pharmaceutical composition is administered to the subject IV, orally or both. In some embodiments of the method, the effect on the neoplasm is an improved result as compared to an effect on the neoplasm of either the at least one anti-cancer agent alone or the one or more modulators alone. In some embodiments of the method, the PARP inhibitor is administered at a dose of about 0.0075 mg/kg to about 20 mg/kg. In some embodiments of the method, the quercetin is administered at a dose of 0.1 g to 2.5 g. In some embodiments of the method, the SPB is administered at a dose of 0.1 g to 40 g. In some embodiments of the method, the EGCG is administered at a dose is 0.1 g to 1.5 g.

In some embodiments, any of the compositions, kits, uses or methods disclosed herein induces apoptosis in vitro in at least one cancer cell line. In some embodiments, the induction of apoptosis by the composition is additive as compared to the induction of apoptosis of each of the anti-cancer agents and at least one modulators alone. In some embodiments, the induction of apoptosis by the composition is synergistic as compared to the induction of apoptosis of each of the anti-cancer agents and at least one modulator alone. In some embodiments, the composition, kit, use and/or method comprises, consists of, or consists essentially of PARP inhibitor as the at least one anti-cancer agent.

In some embodiments, a pharmaceutical composition, kit, use and/or method is provided, wherein the neoplasm is a triple negative breast cancer wherein the triple negative breast cancer is estrogen receptor-negative, progesterone receptor-negative and human epidermal growth factor receptor 2 (HER2/NEU)-negative. In some embodiments of the pharmaceutical composition, kit, use and/or method the neoplasm is a breast cancer in an individual with germline BRCA1 mutation, germline BRCA2 mutation or both. In some embodiments of the pharmaceutical composition, kit, use and/or method the PARP inhibitor is selected from the group consisting of Olaparib, Veliparib, Niraparib, Talazoparib, Rucaparib, CEP-9722, and Iniparib. In some embodiments of the pharmaceutical composition, kit, use and/or method the PARP inhibitor is Olaparib. In some embodiments of the pharmaceutical composition, kit, use and/or method the PARP inhibitor is Olaparib and wherein the amount of Olaparib is 800 mg per day, or about 100 mg to about 800 mg per day. In some embodiments of the pharmaceutical composition, kit, use and/or method the PARP inhibitor is Olaparib and wherein the amount of Olaparib is 800 mg per day, or about 100 mg to about 800 mg per day, and wherein the modulator is EGCG and quercetin. In some embodiments of the pharmaceutical composition, kit, use and/or method the PARP inhibitor is Olaparib and wherein the amount of Olaparib is 800 mg per day, or about 100 mg to about 800 mg per day, and wherein the modulator is quercetin at 0.5 g IV daily, or about 100 mg to about 3 g IV daily and EGCG at 1 g IV daily, or about 100 mg to about 2 g IV daily.

DETAILED DESCRIPTION

Figure 1:
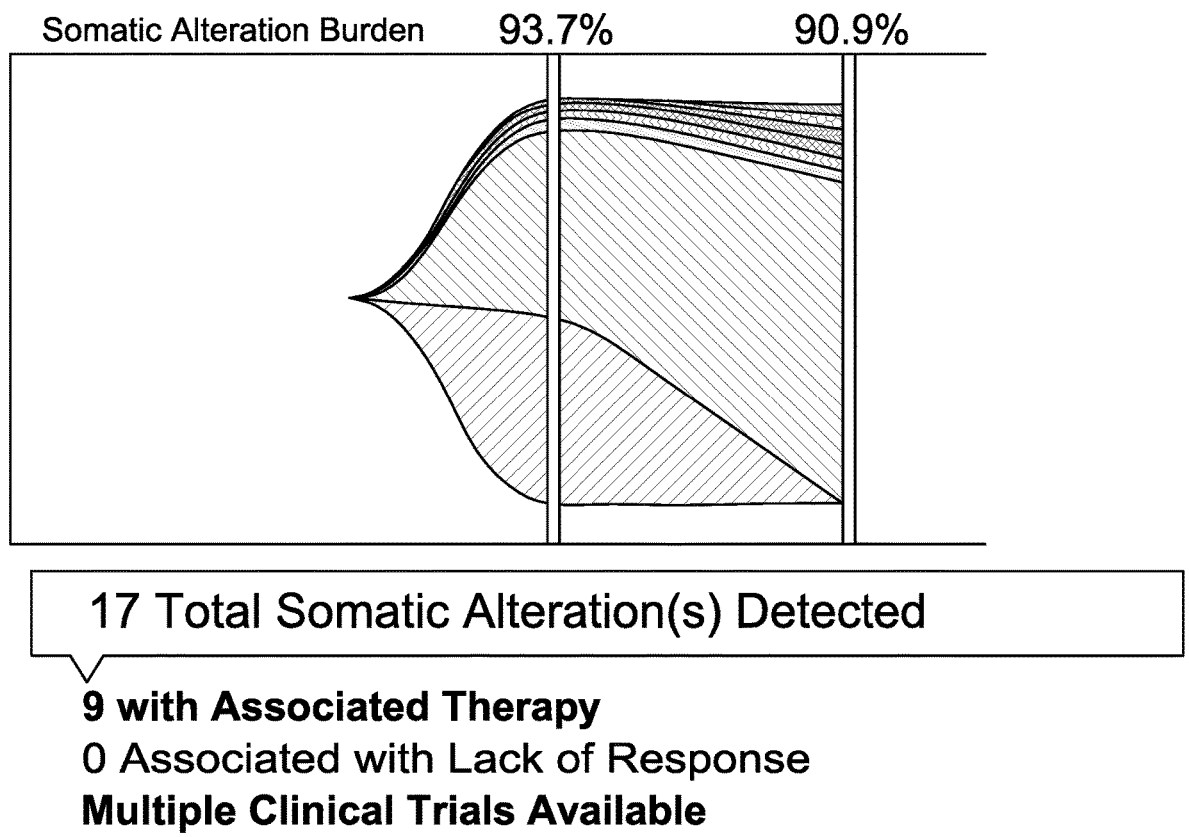
FIG. 1 shows an embodiment of a Guardant360 Tumor Response Map from Test Number 2 (see, Example 4).

Statistics show that deaths caused by advanced cancers of various types have not significantly changed since a decade ago. Indeed, in some cases (e.g., lung cancer) the death rate is rising, especially among women. Even as novel anti-cancer agents are introduced to the market for advanced stages of the disease, patient survival rates have remained essentially unchanged. Moreover, potential toxicity of many novel anti-cancer agents can be a devastating factor both for the clinician and the patient. Additionally, the development of resistance to anti-cancer agents is another cause for concern.

Therefore, compositions, methods, systems and/or kits comprising, consisting of, or consisting essentially of, one or more anti-cancer response modulators in combination with one or more anti-cancer agents for preventing and/or treating neoplasms are provided. In some embodiments, compositions, methods, systems and/or kits comprising, consisting of, or consisting essentially of, one or more anti-cancer response modulators in combination with one or more anti-cancer agents for preventing and/or treating neoplasms that are resistant to the one or more anti-cancer agents are provided. In some embodiments, the at least one anti-cancer agent is a PARP inhibitor.

Also provided herein are embodiments of case studies based on novel combinatorial therapies that provide superior clinical results in a variety of tumor types. In some embodiments, the combinatorial therapies are based on combinations of one or more modulators provided herein and one or more PARP inhibitors provided herein.

Patient Population

Provided herein are embodiments of compositions, methods, systems and/or kits useful for preventing and/or treating one or more neoplasms in patients. A neoplasm could be a tumor, a cancer, any new and/or abnormal growth resembling a tumor and/or cancer, or any combination thereof.

In some embodiments, a patient is administered one or more anti-cancer agents to prevent and/or treat a neoplasm. In some embodiments, the patient is naïve and never been previously treated with one or more anti-cancer agents. In some cases, the patient may initially respond to the one or more anti-cancer agents resulting in an initial regression of the neoplasm. However, the neoplasm may become resistant to the one or more anti-cancer agents resulting in a relapse. In some embodiments, relapse may also occur due to discontinuing treatment, in which case the relapsed neoplasm may or may not be sensitive to the one or more anti-cancer agents previously administered. Therefore, the patient may either be re-administered the same anti-cancer agent or a different anti-cancer agent. In some embodiments, the patient is initially treated with a first anti-cancer agent, but is subsequently treated with a different second anti-cancer agent. This may be due to several reasons including, but not limited to, development of resistance to the first anti-cancer agent, adverse effects of the first anti-cancer agent, etc.

Therefore, the embodiments of the compositions, methods, systems and/or kits provided herein are desirable for patients who are initially responsive but will eventually become non-responsive to one or more anti-cancer agents, or in patients who were initially responsive but have now become non-responsive to one or more anti-cancer agents. The embodiments are also desirable for patients who are non-responsive because they have a neoplasm that is resistant to one or more anti-cancer agents.

In some embodiments, the patient is a male or a female. A patient is typically human but animals other than human are also contemplated. Non-limiting examples of the animals other than human include without limitation domestic animals, pets, experimental animals, and/or commercially important animals.

Tumor and/or Cancer Types

Disclosed herein are non-limiting examples of neoplasms, which could be a tumor, a cancer, any new and/or abnormal growth resembling a tumor and/or cancer, or any combination thereof. In some embodiments, the neoplasm is a breast carcinoma or a breast adenocarcinoma, or any neoplasm associated with breast. In some embodiments, neoplasm is a non-small cell lung carcinoma or lung adenocarcinoma, or any neoplasm associated with lung. In some embodiments, the neoplasm is a uterine sarcoma, or any neoplasm associated with uterus. In some embodiments, the neoplasm is a pancreatic adenocarcinoma, or any neoplasm associated with pancreas. In some embodiments, the neoplasm is a malignant melanoma, or any neoplasm associated with skin. In some embodiments, the neoplasm is a glioblastoma, or any neoplasm associated with brain. In some embodiments, the neoplasm is related to one or more types of neoplasm provided herein.

In some embodiments, the neoplasm is likely to become resistant and/or is already resistant to one or more anti-cancer agents. Thus, the embodiments provided herein are particularly useful for preventing and/or treating neoplasm that are resistant to or are likely to become resistant to one or more anti-cancer agents. In some embodiments, the neoplasm is not resistant and/or is not likely to become resistant to one or more anti-cancer agents. Thus, the embodiments provided herein are useful for preventing and/or treating neoplasm that is not resistant and/or is not likely to become resistant to one or more anti-cancer agents by administering a minimum dose of one or more anti-cancer agents sufficient to prevent and/or treat the neoplasm.

Non-limiting examples of neoplasms include breast adenocarcinoma, pancreatic adenocarcinoma, lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, breast cancer, glioblastoma, or any neoplasm associated with brain including, but not limited to, astrocytomas (e.g., pilocytic astrocytoma, diffuse astrocytoma, anaplastic astrocytoma, and brain stem gliomas), glioblastomas (e.g., glioblastomas multiforme), meningioma, other gliomas (e.g., ependymomas, oligodendrogliomas, and mixed gliomas), and other brain tumors (e.g., pituitary tumors, craniopharyngiomas, germ cell tumors, pineal region tumors, medulloblastomas, and primary CNS lymphomas) (See, cancercenter.com/brain-cancer/types/tab/overview/, which is hereby incorporated by reference in its entirety). In some embodiments, the neoplasm is related to one or more types of neoplasm provided herein.

Anti-Cancer Agents

As used herein an "anti-cancer agent" can be an anti-cancer agent, anti-tumor agent, anti-cancer drug and/or anti-tumor drug that slows the growth, stops the growth, causes a reduction in size, eliminates and/or prevents relapse of a neoplasm. In some embodiments, the anti-cancer agent is a pro-drug.

In some embodiments, the anti-cancer agents are well-known in the art and in some embodiments are approved for therapeutic use and/or use in clinical trials by government agencies (e.g., FDA, EMEA, etc.). The dosing, route of administration, efficacy against known neoplasm types, side/adverse effects, mechanism of action, etc. of the anti-cancer agents may also be well-known in the art. In other embodiments, the anti-cancer agent is a compound that is believed to have anti-cancer effects (e.g., without being limiting, in vitro, in vivo and/or ex vivo in a laboratory and/or in a human clinical trial), but is not yet approved by a government agency for the treatment of cancer.

Anti-Cancer Response Modulators

As used herein an "anti-cancer response modulator" (also referred to herein as "modulator") improves the anti-cancer effect of a known or a novel anti-cancer agent against a neoplasm when used in combination with one or more of the modulators disclosed herein. In some embodiments, the anti-cancer agent may not have any effect in the absence of the modulator. In some embodiments the anti-cancer agent improves the anti-cancer activity of the modulator. In some embodiments, the modulator improves the anti-cancer activity of the anti-cancer agent. In some cases, the two work in concert to improve the anti-cancer activity of each other. In some embodiments, the neoplasm is likely to develop resistance, develops resistance, and/or is already resistant to the known or a novel anti-cancer agent. In some embodiments, the neoplasm is likely to develop resistance, develops resistance, and/or is already resistant to one or more modulators.

Several embodiments of modulators are contemplated. Non-limiting examples of modulators include those that improve the effect of anti-cancer agents including, but not limited to, anti-cancer agents that are effective against one or more types of neoplasm but ineffective against one or more other types of neoplasm.

Thus, modulators are contemplated that improve the effect of anti-cancer agents in a patient who may be non-responsive to a particular anti-cancer agent or the anti-cancer agent may be ineffective in a patient with a particular type of neoplasm even before initiation of treatment with the anti-cancer agent. The modulator can improve the effect of anti-cancer agents in a patient who may initially be responsive to a particular anti-cancer agent or the anti-cancer agent may initially be effective in a patient with a particular type of neoplasm but may eventually become ineffective. In some embodiments, the modulator can improve the effect of anti-cancer agents in a patient with a relapse of the neoplasm.

Non-limiting examples of modulators include quercein, sodium phenyl butyrate (SPB) and epigallocatechin-3-gallate (EGCG). Other modulators are also contemplated. Quercetin is a flavonol found in many fruits, vegetables, leaves, and grains. It can be used as an ingredient in supplements, beverages, or foods. Quercetin is one of the most abundant dietary flavonoids with an average daily consumption of 25-50 mg. Sodium phenyl butyrate is a salt of an aromatic fatty acid, 4-phenylbutyrate (4-PBA) or 4-phenylbutyric acid and is classified by the FDA as an orphan drug for the treatment of urea cycle disorders. Epigallocatechin-3-gallate is a polyphenol and the most abundant catechin in tea. The modulators provided herein are non-toxic and/or minimally toxic with no and/or minimal side effects.

Dose of Modulator

The dose of modulators provided herein are exemplary and not intended to be limiting.

In some embodiments, quercetin is administered intravenously. The concentration of quercetin in a solution for intravenous administration is about 5 mg/ml to about 500 mg/ml. In some embodiments, the concentration of quercetin in a solution for intravenous administration is about 50 mg/ml. In some embodiments, quercetin is administered intravenously at a dose of about 0.05 g to about 10 g. In some embodiments, quercetin is administered intravenously at a dose of about 0.5 g to about 1 g. In some embodiments, quercetin is administered intravenously at a dose of about 0.05, 0.1, 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5 or 10 g, or within a range defined by any two of the aforementioned values.

In some embodiments, quercetin is administered orally. The amount of quercetin in a composition for oral administration is about 100 mg to about 10 g. In some embodiments, quercetin is administered orally at a dose of about 0.5 g to about 4 g. In some embodiments, quercetin is administered orally at a dose of about 1 g. In some embodiments, quercetin is administered orally at a dose of about 0.05, 0.1, 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45 or 50 g, or within a range defined by any two of the aforementioned values. In some embodiments, the composition for oral administration can be prepared into a solution for intravenous administration, wherein the concentration of quercetin is about 10 mg/ml to about 100 mg/ml. In some embodiments, quercetin is administered in a liposomal formulation. In some embodiments, quercetin is administered in a liposomal formulation at 50 mg a day. In some embodiments, quercetin is administered in a liposomal formulation at about 25 mg a day to about 75 mg a day. In some embodiments, quercetin is administered in a liposomal formulation at about 10, 15, 20, 25, 30, 35, 40, 45, 50, 55, 60, 65, 70, 75, 80, 85, 90, 95 or 100 mg a day, or within a range defined by any two of the aforementioned values.

In some embodiments, quercetin by itself is not water soluble and therefore is administered in the oral dosage form. In some embodiments, quercetin in the form of PG/PEG Propylene Glycol quercetin (quercetin PG) is water soluble and is used in the clinic as the IV dosage form.

In some embodiments, SPB is administered intravenously. The concentration of SPB in a solution for intravenous administration is about 20 mg/ml to about 2000 mg/ml. In some embodiments, the concentration of SPB in a solution for intravenous administration is about 200 mg/ml. In some embodiments, SPB is administered intravenously at a dose of about 0.5 g to about 100 g. In some embodiments, SPB is administered intravenously at a dose of about 1 g to about 10 g. In some embodiments, quercetin is administered intravenously at a dose of about 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95 or 100 g, or within a range defined by any two of the aforementioned values.

In some embodiments, SPB is administered orally. The amount of SPB in a composition for oral administration is about 0.1 g to about 50 g. In some embodiments, SPB is administered orally at a dose of about 0.5 g to about 1 g. In some embodiments, SPB is administered orally at a dose of 5 g to about 35 g. In some embodiments, SPB is administered orally at a dose of about 0.1, 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45 or 50 g, or within a range defined by any two of the aforementioned values. In some embodiments, the composition for oral administration can be prepared into a solution for intravenous administration, wherein the concentration of SPB is about 20 mg/ml to about 2000 mg/ml.

In some embodiments, EGCG is administered intravenously. The concentration of EGCG in a solution for intravenous administration is about 5 mg/ml to about 100 mg/ml. In some embodiments, the concentration of EGCG in a solution for intravenous administration is about 20 mg/ml. In some embodiments, EGCG is administered intravenously at a dose of about 0.01 g to about 15 g. In some embodiments, EGCG is administered intravenously at a dose of about 0.1 g to about 1.5 g. In some embodiments, EGCG is administered intravenously at a dose of about 0.01, 0.05, 0.1 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 g, or within a range defined by any two of the aforementioned values.

In some embodiments, EGCG is administered orally. The amount of EGCG in a composition for oral administration is about 0.1 g to about 3 g. In some embodiments, EGCG is administered orally at a dose of about 0.2 g to about 1 g. In some embodiments, EGCG is administered orally at a dose of 0.5 g to about 2.5 g. In some embodiments, EGCG is administered orally at a dose of about 0.1 0.2, 0.3, 0.4, 0.5, 0.6, 0.7, 0.8, 0.9, 1, 1.5, 2, 2.5 or 3 g, or within a range defined by any two of the aforementioned values. In some embodiments, the composition for oral administration can be prepared into a solution for intravenous administration, wherein the concentration of EGCG is about 5 mg/ml to about 100 mg/ml. In some embodiments, a preventive dose of EGCG is about 0.27 g administered 2 times a day. In some embodiments, a preventive dose of EGCG is about 0.27 g administered 3 times a day.

Combinations

A surprising and unexpected anti-cancer effect was observed when one or more anti-cancer agents were used in combination with one or more modulators provided herein. The surprising and unexpected result was a better than expected result wherein the effectiveness of the one or more anti-cancer agents was improved when used in combination with one or more modulators as compared to the anti-cancer agent in the absence of the modulator(s). The potentiation was achieved by co-administering the one or more anti-cancer agents and one or more modulators.

Therefore, provided herein are combinations of one or more anti-cancer agents and one or more modulators. The one or more modulators can improve the effect of one or more anti-cancer agent against one or more neoplasm types provided herein. The potentiation can occur in several ways. Non-limiting examples include enhancing the effectiveness of an already effective anti-cancer agent, making an ineffective anticancer agent effective (the anticancer agent could also have been previously effective but become ineffective following long term and/or short term use in a patient), increasing the length of time for which an anti-cancer agent is effective, decreasing the effective dose of administration of the anti-cancer agent, decreasing the duration of time for which anti-cancer agent is administered, decreasing the frequency of administration of an anti-cancer agent, and/or enabling the administration of anti-cancer agent via a more amenable route.

The one or more anti-cancer agents can be provided at any dose, via any of the routes of administration, in any order of administration, at any frequency of administration, and/or any dosage form provided herein. Similarly, the one or more modulators can be provided at any dose, via any of the routes of administration, in any order of administration, at any frequency of administration, and/or any dosage form provided herein. Also, the combination of one or more anti-cancer agent and one or more modulators can be provided at any dose, via any of the routes of administration, in any order of administration, at any frequency of administration, and/or any dosage form provided herein.

Combinations can comprise, consist of, or consist essentially of, one or more anti-cancer agents and one or more modulators. In some embodiments, the combination comprises, consists of, or consists essentially of, one or more anti-cancer agents and one modulator selected from the group consisting of quercetin, SPB and EGCG. In some embodiments, the modulator is quercetin. In some embodiments, the modulator is SPB. In some embodiments, the modulator is EGCG. In some embodiments, the combination comprises, consists of, or consists essentially of, one or more anti-cancer agents and at least one modulator. In some embodiments, the at least one modulator is selected from the group consisting of quercetin, SPB and EGCG. For example; in some embodiments, the combination can comprise, consist of, or consist essentially of, the anticancer agent and quercetin, or the anti-cancer agent and SPB, or the anti-cancer agent and EGCG. In some embodiments, the combination comprises, consists of, or consists essentially of, one or more anti-cancer agents and at least two modulators. In some embodiments, the at least two modulators are selected from the group consisting of quercetin, SPB and EGCG. For example, in some embodiments, the combination can comprise, consist of, or consist essentially of, the anticancer agent and quercetin and SPB as the modulators, or the anti-cancer agent and quercetin and EGCG as the modulators, or the anti-cancer agent and SPB and EGCG as the modulators. In some embodiments, the anti-cancer agent is PARP inhibitor.

In some embodiments, the combination may comprise, consist of, or consist essentially of, one or more additional modulators, for example, a third modulator selected from the group consisting of quercetin, SPB and EGCG. In some embodiments, if the first two modulators are quercetin and SPB, the third modulator is EGCG, if the first two modulators are quercetin and EGCG, the third modulator is SPB, and if the first two modulators are SPB and EGCG, the third modulator is quercetin. Therefore, for example, the combination can comprise, consist of, or consist essentially of, the anticancer agent and quercetin, SPB and EGCG as the three modulators. In some embodiments, the anti-cancer agent is PARP inhibitor.

The potentiation can be additive or synergistic. A synergistic effect is greater than an additive effect. An additive effect is observed when the potentiation is equal to the sum of the individual effects of the anti-cancer agent(s) and modulator(s). A synergistic effect is observed when the potentiation is greater than the sum of the individual effects of the anti-cancer agent and modulator(s). Synergistic effect, additive effect or both can be occur human patients, non-human patients, non-patient human volunteers, in vivo models, ex vivo models, in vitro models, etc.

Potentiation can range from about ≤1 to about 100 fold. In some embodiments, the synergistic effect is about 3 to about 30 fold. In some embodiments, the potentiation ranges from <1, 1, >1, 2, 3, 4, 5, 6, 7, 8, 9, 10, 20, 30, 40, 50, 60, 70, 80, 90, or 100 fold, or within a range defined by any two of the aforementioned values. In some embodiments, a synergistic effect allows for a reduction in the requirement of an anti-cancer agent to about 25% to about 75% of the recommended dose. In some embodiments, a synergistic effect allows for a reduction in the requirement of an anti-cancer agent to about 5, 10, 20, 30, 40, 50, 60, 70, 80, 90, or 95% of the recommended dose, or a value within a range defined by any two of the aforementioned values.

For example, the combination of PARP inhibitor with quercetin and SPB can produce a synergistic effect on a neoplasm that is resistant to PARP inhibitor alone.

In some embodiments, additive and/or synergistic or sustained response to a combinational therapy is observed. In some embodiments, "combination therapy" is intended to encompass administration of these therapeutic agents in a sequential manner, wherein each therapeutic agent is administered at a different time, as well as administration of these therapeutic agents, or at least two of therapeutic agents concurrently, or in a substantially simultaneous manner. Simultaneous administration can be accomplished, for example, by administering to the subject a single dosage form, for example, a solution, pill or capsule, having a fixed ratio of each therapeutic agent or in multiple, single dosage forms for each of therapeutic agents. Sequential or substantially simultaneous administration of each therapeutic agent can be effected by any appropriate route including, but not limited to, oral routes, intravenous routes, intramuscular routes, and direct absorption through mucous membrane tissues.

In some embodiments, mixtures of compositions of the present invention can also be administered to the patient as a simple mixture or in suitable formulated pharmaceutical compositions. In some embodiments, combination therapy can be achieved by administering two or more agents, e.g., two or more other therapeutic agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The potentiation can be measured in one or more assays that measure effects such as apoptosis, cellular metabolic changes, cellular morphological changes, etc., or other effects that would be well-known to one of ordinary skill in the art. In some embodiments, the combination of anti-cancer agent(s) and one or more modulators causes an induction of apoptosis, which can be measured using the MiCK® assay. In some embodiments, the modulator can suppress angiogenesis within/around the neoplasm. For example, quercetin causes suppression of angiogenesis in glioma cells.

In some embodiments, the one or more modulators provided herein are effective as anticancer agents without the presence of an anti-cancer agent. Thus, in some embodiments, the one or more modulators provided herein are independently effective as anti-cancer agents, i.e., without co-administration of one or more anti-cancer agents.

However, when the one or more modulators provided herein are administered in combination with one or more anti-cancer agents, a synergistic anti-cancer effect is observed. Thus, in some embodiments, a synergistic anti-cancer effect is observed when the one or more modulators provided herein are co-administered with the one or more anti-cancer agents provided herein. For example, a synergistic anti-cancer effect is observed when quercetin (e.g. as quercetin PG is co-administered with PARP inhibitor (See, Examples 4-6).

Route of Administration

The route of administration of the modulator(s) and anti-cancer agent(s) can be determined by one of ordinary skill in the art based on the circumstances. Several non-limiting routes of administrations are possible including parenteral, subcutaneous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

Any route of administration provided herein can be used for the combination of anti-cancer agent(s) and modulator(s) or for the individual components of the combination. For example, the combination of anti-cancer agent and modulator can be administered intravenously, orally or both. In some embodiments, one or more components in the combination can be administered via one route (e.g., intravenously) and the other components can be administered via a different route (e.g., orally). In some embodiments, all components in the combination are administered via the same route (e.g., either intravenously or orally). The anti-cancer agent and modulators can be administered via any combination of intravenous and oral routes as shown in the non-limiting examples of Table 1 and Table 2.

TABLE 1

Combinations comprising, consisting of, or consisting essentially of, one anti-cancer agent and two modulators (S1, S2)

| | Route of administration | | |
|---|---|---|---|
| Combination | Anti-cancer agent | S1 | S2 |
| 1 | IV | IV | IV |
| 2 | Oral | IV | IV |
| 3 | IV | Oral | IV |

TABLE 1-continued

Combinations comprising, consisting of, or consisting essentially of, one anti-cancer agent and two modulators (S1, S2)

| Combination | Route of administration | | |
|---|---|---|---|
| | Anti-cancer agent | S1 | S2 |
| 4 | IV | IV | Oral |
| 5 | Oral | Oral | IV |
| 6 | Oral | IV | Oral |
| 7 | IV | Oral | Oral |
| 8 | Oral | Oral | Oral |

TABLE 2

Combinations comprising, consisting of, or consisting essentially of, one anti-cancer agent and three modulators (S1, S2, S3)

| Combination | Route of administration | | | |
|---|---|---|---|---|
| | Anti-cancer agent | S1 | S2 | S3 |
| 1 | IV | IV | IV | IV |
| 2 | Oral | IV | IV | IV |
| 3 | IV | Oral | IV | IV |
| 4 | IV | IV | Oral | IV |
| 5 | IV | IV | IV | Oral |
| 6 | Oral | Oral | IV | IV |
| 7 | Oral | IV | Oral | IV |
| 8 | Oral | IV | IV | Oral |
| 9 | IV | Oral | Oral | IV |
| 10 | IV | Oral | IV | Oral |
| 11 | IV | IV | Oral | Oral |
| 12 | Oral | Oral | Oral | IV |
| 13 | IV | Oral | Oral | Oral |
| 14 | Oral | IV | Oral | Oral |
| 15 | Oral | Oral | IV | Oral |
| 16 | Oral | Oral | Oral | Oral |

In some embodiments of Table 1 and Table 2, the anti-cancer agent is PARP inhibitor, S1 is quercetin, S2 is SPB, and S3 is EGCG.

Order of Administration

Any order of administration can be used for the one or more anti-cancer agents and one or more modulators in a combination. For example, the one or more anti-cancer agents and the one or more modulators in the combination can be administered simultaneously or sequentially. For example, all components of the combination are administered simultaneously, or only some of the components of the combination are administered simultaneously and the rest are administered sequentially. In some embodiments, none of the components are administered simultaneously, i.e., all the components are administered sequentially. When administering sequentially, any order of administration can be used. For example, when administering a combination of one anti-cancer agent and two modulators, the anti-cancer agent can be administered first followed by the two modulators either simultaneously or sequentially in any order, or the two modulators can be administered first either simultaneously or sequentially in any order followed by the anti-cancer agent, or one of the modulator each can be administered before and after the administration of the anti-cancer agent. Additional orders of administration are possible and contemplated when the combination comprises, consists of, or consists essentially of, additional components, for example, a third modulator.

Frequency of Administration

Frequency of administration of the anti-cancer agent is as known in the art. Frequency of administration of the anti-cancer agent can be varied depending various parameters such as level of potentiation, prognosis following administration of a combination provided herein, patient compliance, side effects, etc., for example, daily, weekly, biweekly, monthly, bimonthly, or as is known in the art. Modulators can be administered along with the anti-cancer agent daily, weekly, biweekly, monthly, bimonthly, less frequently compared to the anti-cancer agent, or more frequently compared to the anti-cancer agent.

Administration can be daily, or 1, 2, 3, 4, 5, 6 or more times weekly, or more or less frequently as required. Administration can be provided as a single dose or as divided doses, such that a daily dose may be given in 2, 3, 4, or more portions in a single day.

Co-administration of the components of a combination may comprise administering the components simultaneously, or within about 1, 5, 15, 30, 45 or 60 minutes of one another, or within any range defined by the aforementioned values. Co-administration of the components of a combination may comprise, consist of, or consist essentially of, administering the components within about 1 hour to within about 6 hours of one another, or within any range defined by the aforementioned values.

Pharmaceutical Formulations

In some embodiments, pharmaceutical formulations for prophylaxis, treatment or both of a neoplasm are provided. The formulation can be a single composition for co-administration comprising, consisting of, or consisting essentially of, at least one anti-cancer agent and one, two, three or more modulators. In some embodiments, the formulation comprises, consisting of, or consisting essentially of, more than one composition, e.g. the anti-cancer agent in one dosage form, and the one or more modulators in a second, third or fourth dosage form. Several compositions are contemplated. The type of composition to be administered can be determined by one of ordinary skill in the art based on the circumstances under which administration is desired.

The compositions provided herein comprise, consist of, or consist essentially of, active ingredients, inactive ingredients, excipients, additives, and/or pharmaceutically acceptable carriers. Examples of additives include natural polymer compounds, inorganic salts, binders, lubricants, disintegrants, surfactants, thickeners, coating agents, pH adjusters, antioxidants, flavoring agents, preservatives, and colorants among others. Examples of other pharmaceutically acceptable carriers include liquid carriers such as water, alcohol, emulsion, and solid carriers such as gel, powder, etc. Standard pharmaceutical formulation techniques and ingredients can be used, such as those disclosed in Remington's The Science and Practice of Pharmacy, 21st Ed., Lippincott Williams & Wilkins (2005), which is hereby incorporated by reference in its entirety.

Compositions for intravenous administration comprise, consist of, or consist essentially of, excipient and pharmaceutically acceptable carries including one or more of sodium chloride, dextrose, and sterile water. Compositions can comprise, consist of, or consist essentially of, aqueous isotonic sterile injection solutions, which can comprise, consist of, or consist essentially of, one or more of antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Compositions for oral administration can be any dosage form that is suitable for oral ingestion, for example, liquid compositions such as elixir, suspension, syrup, emulsion, ampoule, etc., solid compositions such as gel, gum, drop, powder, granule, pill, sugar-coated tablet, film-coated tablet, capsule, package agent, etc. Also contemplated are sustained-release compositions such as gel-coated compositions, multi-coated compositions, localized release compositions.

In some embodiments, the compositions are administered by intravenous infusion. The compositions can be presented in unit-dose or multi-dose sealed containers, such as ampules and/or vials. Injection solutions and suspensions can be prepared from sterile powders, granules, and/or tablets. In some embodiments, the compositions to be administered can be formulated as pharmaceutical formulations for delivery via one or more of the routes provided herein.

A composition can comprise, consist of, or consist essentially of, a combination of one or more anti-cancer agents and one or more modulators, wherein the one or more anti-cancer agents and one or more modulators can be present in any dosage form. For example, in a composition comprising a, combination of one anti-cancer agent and two modulators, all three components can be in the same dosage form (e.g., for intravenous administration or for oral administration), or one of the components in the combination can be of one dosage form (e.g., for intravenous administration or for oral administration) and other two component in the combination can be of a different dosage form (e.g., for intravenous administration or for oral administration). In some embodiments, all three components in the combination may be of a different, dosage form (e.g., for intravenous administration, for oral administration, and a third dosage form). In some embodiments, when the combination additionally comprises, consists of, or consists essentially of, a third modulator, the dosage form of the third modulator may be the same as one of the other components in the combination or the third modulator may be present in a different (e.g., fourth) dosage form. The various dosage forms can be administered in an order as disclosed herein.

In some embodiments, the pharmaceutical formulation is formulated as one or more of a nanoparticle formulation, a liposomal formulation, or folic acid receptor conjugates. Nanoparticle formulations have many advantages over traditional dosage forms, such as enhanced dissolution properties and potential for efficient intracellular delivery of drugs. Nanoparticles have unique physical and chemical properties that offer several advantages as drug delivery carriers, or 'nano-carriers.' Nanoparticles-based composition for detection and/or treatment of cancers can comprise nanoparticles in the form of, without limitations, quantum dots, magnetic nanoparticles, gold nanoshells (which are useful in detecting tumors and metastasis in many solid tumors), poly (lactide-co-glycolide) (PLGA)-based nanoparticles (e.g., PLGA/montmorillonite (PLGA/MMT) nanoparticles, Vitamin E-TPGS-emulsified PLGA nanoparticles, PLGA-mPEG nanoparticles), dendrimers, and SPIO and USPIO nanoparticles. See, Mousa S. A. and Bharali D. J., *Nanotechnology-Based Detection and Targeted Therapy in Cancer: Nano-Bio Paradigms and Applications*, Cancers (Basel), Vol. 3, No. 3, pp. 2888-2903, September 2011, which is hereby incorporated by reference in its entirety. Other nanoparticle-based examples are provided in Bharali D. J. and Mousa S. A., *Emerging nanomedicines for early cancer detection and improved treatment: current perspective and future promise*, Pharmacology & Therapeutics, Vol. 128, No. 2, pp. 324-335, November 2010, and Bharali D. J., et al., *Nanoparticles and cancer therapy: a concise review with emphasis on dendrimers*, International Journal of Nanomedicine, Vol. 4, pp. 1-7, Apr. 1, 2009, which are hereby incorporated by reference in their entirety. Pharmaceutical compositions can also be formulated as nano-micelles-based compositions, for example, as provided in U.S. Pat. No. 9,308,270 B2, which is hereby incorporated by reference in its entirety. Folic acid receptor conjugates based on a conjugating a molecule/drug with folic acid to form a "folate conjugate." Owing to the naturally high affinity of folate for the folate receptor protein commonly expressed on the surface of many human cancers, folate conjugates bind tightly to the folate receptor protein and trigger cellular uptake via endocytosis. Diverse molecules/drugs can be successfully delivered inside folate receptor protein expressing cells and tissues. Liposomal formulations comprise liposomes that are used as vehicles for administration of drugs. Liposomes are most often composed of phospholipids, especially phosphatidylcholine, but may also include any lipids that are compatible with a lipid bilayer structure (e.g., as egg phosphatidylethanolamine). A liposomal formulation can comprise liposomes that may employ surface ligands for attaching to unhealthy tissue. The major types of liposomes are multilamellar vesicle with several lamellar phase lipid bilayers, small unilamellar liposome vesicle with one lipid bilayer, large unilamellar vesicle, and cochleate vesicle.

For example, in a composition comprising a combination of PARP inhibitor as the anti-cancer agent and quercetin and SPB as the two modulators, all three can be in an intravenous or oral dosage form, PARP inhibitor can be in an intravenous dosage form and quercetin and SBP can be in an oral dosage form, or PARP inhibitor can be in oral dosage form and quercetin and SPB can be in an intravenous dosage form. In some embodiments, the combination may comprise a third modulator (e.g., EGCG) that is in the same or a different dosage form than the anti-cancer agent and/or one or more of the modulators.

Kits

Inasmuch as it may desirable to administer one or more combinations provided herein, for example, for the purpose of preventing and/or treating a neoplasm, it is within the scope of the present disclosure to provide the components of a combination as a kit such that the components of the combination are suitable for co-administration.

A kit comprising, consisting of, or consisting essentially of, one or more anti-cancer agents to be used in combination with one or more modulators is provided.

In some embodiments, the kit comprises one anti-cancer agent to be used in combination with two modulators. In some embodiments, the kit further comprises, consists of, or consists essentially of, a third modulator. Thus, the kit comprises, consists of, or consists essentially of, one anti-cancer agent to be used in combination with three modulators.

The components can be separately provided such as in separate containers, or in separate compartments of a divided bottle or divided foil packet (e.g., a blister pack used for the packaging of tablets, capsules, etc.).

The kit is particularly suitable for administering different dosage forms, for example, oral and intravenous, for administering the components at different dosage intervals, and/or for titration of components against one another. The kit typically comprises, consists of, or consists essentially of, directions for administration and may additionally be provided with a memory aid to ensure compliance.

The components in the kit may exist in dissolved form, undissolved form or a combination thereof. If present in undissolved form, the undissolved component may be combined with another component present in a dissolved form in a specific stoichiometric amount prior to use. If all the components are present in an undissolved form, the components can either be administered as such (e.g., orally) or dissolved into a solvent (e.g., water) prior to administration (e.g., intravenously).

In some embodiments, the kit comprises PARP inhibitor as the anti-cancer agent to be used in combination with quercetin and SPB as the two modulators. In some embodiments, the kit can comprise EGCG as the third modulator. Thus, the kit comprises PARP inhibitor as the anti-cancer agent to be used in combination with quercetin, SPB and EGCG as the three modulators.

PARP Inhibitor

Several PARP inhibitors are currently under development for BRCA positive tumors (Table 3).

TABLE 3

PARP inhibitors

| PARP Inhibitor | Manufacturer | Clinical Trial Status |
| --- | --- | --- |
| Olaparib (AZD2281) | AstraZeneca | Phase 3 studies in adjuvant and advanced settings in germline BRCAm breast cancer |
| Veliparib (ABT-888) | Abbvie | Phase 3 study in neoadjuvant setting in combination with carboplatin and standard therapy in triple-negative breast cancer<br>Phase 2/3 studies in advanced setting as combination therapy in germline BRCAm breast cancer |
| Niraparib (formerly MK-4827) | Tesaro | Phase 3 study in advanced setting in germline BRCAm breast cancer |
| Talazoparib (BMN-673) | BioMarin Pharmaceuticals | Phase 3 study in advanced setting in germline BRCAm breast cancer<br>Phase 2 studies in advanced setting in BRCAm breast cancer<br>Phase 2 study in advanced setting in germline BRCA intact breast cancer<br>Phase 2 study in neoadjuvant setting in BRCAm breast cancer |
| Rucaparib (formerly AG-14699) | Clovis Oncology | Phase 2 study in advanced setting in patients with known germline BRCAm solid tumors<br>Phase 2 study in adjuvant setting in triple-negative breast cancer or germline BRCAm breast cancer |
| CEP-9722 | Teva Pharmaceutical Industries | Phase 2 study in advanced setting in solid tumors |
| Iniparib | Sanofi | |

However, a treatment approach based on PARP, inhibitors has shown promising results only for a short duration of time in the majority of cases due to secondary mutations and promoter gene methylation. Most patients with triple negative breast cancer when treated with such agents only benefit for a short time, until the tumor shows resistance and eventually the therapy fails.

PARP inhibitors applied in phase III trials for triple negative breast cancer have failed to produce significant improvement in overall survival. A good example of this is phase III trial using Iniparib in patients with triple negative breast cancer who also received cytotoxic chemotherapy and showed no improvement in survival, even though phase II trial showed promising results. A common rationale on the failure of the drug is the epigenetic aberrancies involving the BRCA gene and acquired resistance explained by secondary mutations.

Without being bound by any theory, preclinical results showed a correlation between the efficacy of PARP inhibitors and the intensity with which and duration for which the PARP enzyme is "trapped" at certain DNA damage sites. See, hopkinsmedicine.org/news/media/releases/epigenetic_drug_may_boost_success_of_parp_inhibitor_treatment_for_certain_leukemias_and_breast_cancers, which is hereby incorporated by reference in its entirety.

Therefore, it is believed that increasing the duration and intensity of this "trapping" by combining PARP inhibitors and one or more of the modulators disclosed herein, one could potentially increase the efficacy of PARP inhibitors. In a preferred embodiment, the combination is used for treatment of an advanced case of triple negative breast cancer.

In any of the embodiments disclosed herein, the anti-cancer agent can be one or more PARP inhibitors provided in Table 3. In addition to their use in cancer therapy, PARP inhibitors are considered a potential treatment for acute life-threatening diseases, such as stroke and myocardial infarction, as well as for long-term neurodegenerative diseases.

In any of the embodiments of the methods, systems and/or kits disclosed herein, the embodiments of the compositions can be used for the treatment of diseases, including but not limited to types of cancers disclosed herein and any other diseases or cancers known in the art to be treated by the disclosed compounds. In any of the embodiments of the compositions, methods, systems and/or kits disclosed herein, the anti-cancer agent can be PARP inhibitor.

The dosing of PARP inhibitor varies depending on, among other aspects, type of PARP inhibitor, patient age, route of administration, neoplasm type, etc. PARP inhibitor is typically administered intravenously, orally or both in adult and pediatric patients.

Non-limiting examples of PARP inhibitors are provided in Table 3. Non-limiting examples of treatment regimens with PARP inhibitors include Rucaparib at 600 mg orally twice daily, Veriparib at 600 mg orally twice daily, Talazoparib at >0.5 mg orally once daily, Niraparib at 300 mg once daily, Olaparib at a recommended dose of 400 mg (8×50 mg capsules) taken orally twice daily (800 mg per day), Iniparib at 10 mg/kg to 70 mg/kg daily, and CEP 9722 at 150 mg a day.

In some embodiments, the amount of PARP inhibitor ranges between about 0.5 mg and about 1200 mg per day. In some embodiments, the amount of PARP inhibitor ranges between about 0.1 mg and about 6000 mg per day. In some embodiments, the amount of PARP inhibitor is about 0.1, 0.25, 0.5, 0.75, 1, 2.5, 5, 7.5, 10, 25, 50, 75, 100, 250, 500, 750, 1000, 1500, 2000, 2500, 3000, 3500, 4000, 4500, 5000, 5500 or 6000 mg per day, or within a range defined by any two of the aforementioned values. In some embodiments the dose of PARP inhibitor is about 0.0075 mg/kg to about 20 mg/kg. In some embodiments the dose of PARP inhibitor is about 0.0015 mg/kg to about 100 mg/kg. In some embodiments the dose of PARP inhibitor is about 0.0015, 0.003, 0.006, 0.012, 0.024, 0.036, 0.048, 0.060, 0.072, 0.084, 0.096, 0.2, 0.25, 0.5, 0.75, 1, 2, 3, 6, 12, 18, 24, 30, 40, 50, 60, 70, 80, 90 or 100 mg/kg, or within a range defined by any two of the aforementioned values.

In some embodiments, the frequency of administration is daily. In some embodiments, the frequency of administration is once a week. In some embodiments, the frequency of administration is once every two weeks. In some embodiments, the frequency of administration is once every three weeks. In some embodiments, the frequency of administration can be dose is once every 6 months. In some embodiments, the frequency of administration can be adjusted as desired by one of ordinary skill in the art based on parameters such as the type of drug, the route of administration, the disease, and the like.

Other regimens of intravenous and oral PARP inhibitor have also been reported. Dosages must be adjusted in accord with objective indicator for regulating dosage, for example, evidence of antitumor activity, leukopenia or both. Total leukocyte count is a good, objective indicator for regulating dosage.

PARP inhibitor is effective alone for susceptible malignancies. However, PARP inhibitor can be used concurrently or sequentially with one or more other PARP inhibitors and/or other antineoplastic drugs. When PARP inhibitor is included in combined cytotoxic regimens, the doses of PARP inhibitor as well as that of the other drugs are adjusted accordingly as known to those of skill in the art.

The compositions, methods, systems and/or kits provided herein can be used for treating neoplasms, non-limiting examples of which are malignant lymphomas (Stages III and IV of the Ann Arbor staging system), Hodgkin's disease, lymphocytic lymphoma (nodular or diffuse), mixed-cell type lymphoma, histiocytic lymphoma, Burkitt's lymphoma, multiple myeloma, leukemias including but not limited to chronic lymphocytic leukemia, chronic granulocytic leukemia (it is usually ineffective in acute blastic crisis), acute myelogenous and monocytic leukemia, acute lymphoblastic (stem-cell) leukemia, mycosis fungoides (advanced disease), neuroblastoma (disseminated disease), adenocarcinoma of the ovary, retinoblastoma, carcinoma of the breast, triple negative breast cancer, and biopsy-proven minimal change nephrotic syndrome in pediatrics patients who failed to adequately respond to or are unable to tolerate adrenocorticosteroid therapy. Additional FDA approved and off label indications for PARP inhibitor are ovarian cancer, retinoblastoma, breast cancer, multiple myeloma, Ewing sarcoma, rhabdomyosarcoma, endometrial cancer, lung cancer, as well as melanomas, hematological malignancies, squamous cell carcinomas, prostate cancer and pancreatic cancer.

Provided herein are combinations comprising PARP inhibitor and at least one modulator selected from the group consisting of quercetin, SPB and EGCG. In some embodiments, the combination comprises, consists of, consists essentially of, PARP inhibitor and quercetin. In some embodiments, the combination comprises, consists of, consists essentially of, PARP inhibitor and SPB. In some embodiments, the combination comprises, consists of, consists essentially of, PARP inhibitor and EGCG. The combinations can comprise, consist of, consist essentially of, PARP inhibitor, quercetin, SPB and EGCG at any of the doses provided herein for each.

Also provided are combinations comprising PARP inhibitor and at least two modulators selected from the group consisting of quercetin, SPB and EGCG. In some embodiments, the combination comprises, consists of, consists essentially of, PARP inhibitor, quercetin and SPB. In some embodiments, the combination comprises, consists of, consists essentially of, PARP inhibitor, quercetin and EGCG. In some embodiments, the combination comprises, consists of, consists essentially of, PARP inhibitor, SPB and EGCG. The combinations can comprise, consist of, consist essentially of, PARP inhibitor, quercetin, SPB and EGCG at any of the doses provided herein for each.

In some embodiments, the combination comprises, consists of, consists essentially of, PARP inhibitor and three modulators. In some embodiments, the combination comprises, consists of, consists essentially of, PARP inhibitor, quercetin, SPB and EGCG. The combinations can comprise, consist of, consist essentially of, PARP inhibitor, quercetin, SPB and EGCG at any of the doses provided herein for each. In some embodiments, the combination comprises, consists of, consists essentially of, one or more additional anti-cancer agents and one or more additional modulators.

Non-limiting examples of PARP inhibitors are provided in Table 3. Non-limiting examples of treatment regimens with PARP inhibitors include Rucaparib at 600 mg orally twice daily, Veriparib at 600 mg orally twice daily, Talazoparib at ≥0.5 mg orally once daily, Niraparib at 300 mg once daily, Olaparib at a recommended dose of 400 mg (8×50 mg capsules) taken orally twice daily (800 mg per day), Iniparib at 10 mg/kg to 70 mg/kg daily, and CEP 9722 at 150 mg a day.

In some embodiments, the amount of PARP inhibitor ranges between about 0.5 mg and about 1200 mg per day. In some embodiments, the amount of PARP inhibitor ranges between about 0.1 mg and about 6000 mg per day. In some embodiments, the amount of PARP inhibitor is about 0.1, 0.25, 0.5, 0.75, 1, 2.5, 5, 7.5, 10, 25, 50, 75, 100, 250, 500, 750, 1000, 1500, 2000, 2500, 3000, 3500, 4000, 4500, 5000, 5500 or 6000 mg per day, or within a range defined by any two of the aforementioned values. In some embodiments the dose of PARP inhibitor is about 0.0075 mg/kg to about 20 mg/kg. In some embodiments the dose of PARP inhibitor is about 0.0015 mg/kg to about 100 mg/kg. In some embodiments the dose of PARP inhibitor is about 0.0015, 0.003, 0.006, 0.012, 0.024, 0.036, 0.048, 0.060, 0.072, 0.084, 0.096, 0.2, 0.25, 0.5, 0.75, 1, 2, 3, 6, 12, 18, 24, 30, 40, 50, 60, 70, 80, 90 or 100 mg/kg, or within a range defined by any two of the aforementioned values.

Doses of quercetin, SPB and EGCG for intravenous administration can be any one of the doses provided herein. For example, doses of quercetin for intravenous administration include, without limitations, 0.5 g to 1 g. Doses of SPB for intravenous administration include, without limitations, 5 g to 10 g. Doses of EGCG for intravenous administration include, without limitations, 0.1 g to 1.5 g.

In some embodiments, the any of the combinations herein are provided as compositions, methods and/or kits for preventing neoplasms in patients and/or treating neoplasms in patients. Any of the doses, routes of administration, frequency of administration, sequence of administration, etc. provided herein can be used for the components of the combinations.

The dose, route of administrations, mechanism of action, etc. of PARP inhibitor are well-known in the art. The dose of PARP inhibitor can be varied depending on, among other aspects, patient age, route of administration, neoplasm type, etc.

Additional Embodiments

In some embodiments, the combinations in the compositions, and the compositions for the kits, uses and/or methods described herein comprise, consist of, or consist essentially of, quercetin+PARP inhibitor, wherein quercetin is administered intravenously, wherein the concentration of quercetin in a solution for intravenous administration is about 5 mg/ml to about 500 mg/ml, and wherein PARP inhibitor is administered orally, wherein the PARP inhibitor is in a solution for oral administration.

In some embodiments, the combinations in the compositions, and the compositions for the kits, uses and/or methods described herein comprise, consist of, or consist essentially of, quercetin+PARP inhibitor, wherein quercetin is administered intravenously, wherein the dose of quercetin in a solution for intravenous administration is about 0.05 g to about 10 g, and wherein PARP inhibitor is administered orally, wherein the PARP inhibitor is in a solution for oral administration.

In some embodiments, the combinations in the compositions, and, the compositions for the kits, uses and/or methods described herein comprise, consist of, or consist essentially of, quercetin+PARP inhibitor, wherein quercetin is administered orally, wherein the amount of quercetin in a composition for oral administration is about 100 mg to about 50 g, and wherein PARP inhibitor is administered orally, wherein the PARP inhibitor is in a composition for oral administration.

In some embodiments, the combinations in the compositions, and the compositions for the kits, uses and/or methods described herein comprise, consist of, or consist essentially of, quercetin+PARP inhibitor, wherein quercetin is administered in a liposomal formulation, wherein the dose of: quercetin for administration in a liposomal formulation is about 25 mg a day to about 100 mg a day, and wherein PARP inhibitor is either administered orally, wherein the PARP inhibitor is in a solution for oral administration.

In some embodiments, the combinations in the compositions, and the compositions for the kits, uses and/or methods described herein comprise, consist of, or consist essentially of, SPB+PARP inhibitor, wherein SPB is administered intravenously, wherein the concentration of SPB in a solution for intravenous administration is about 20 mg/ml to about 2000 mg/ml, and wherein PARP inhibitor is administered orally, wherein the PARP inhibitor is in a solution for oral administration.

In some embodiments, the combinations in the compositions, and the compositions for the kits, uses and/or methods described herein comprise, consist of, or consist essentially of, SPB+PARP inhibitor, wherein SPB is administered intravenously, wherein the dose of SPB in a solution for intravenous administration is about 0.5 g to about 100 g, and wherein PARP inhibitor is administered orally, wherein the PARP inhibitor is in a solution for oral administration.

In some embodiments, the combinations in the compositions, and the compositions for the kits, uses and/or methods described herein comprise, consist of, or consist essentially of, SPB+PARP inhibitor, wherein SPB is administered orally, wherein the amount of SPB in a composition for oral administration is about 0.1 g to about 50 g, and wherein PARP inhibitor is administered orally, wherein the PARP inhibitor is in a composition for oral administration.

In some embodiments, the combinations in the compositions, and the compositions for the kits, uses and/or methods described herein comprise, consist of, or consist essentially of, EGCG+PARP inhibitor, wherein EGCG is administered intravenously, wherein the concentration of EGCG in a solution for intravenous administration is about 5 mg/ml to about 100 mg/ml, and wherein PARP inhibitor is administered orally, wherein the PARP inhibitor is in a solution for oral administration.

In some embodiments, the combinations in the compositions, and the compositions for the kits, uses and/or methods described herein comprise, consist of, or consist essentially of, EGCG+PARP inhibitor, wherein EGCG is administered intravenously, wherein the dose of EGCG in a solution for intravenous administration is at a dose of about 0.01 g to about 15 g, and wherein PARP inhibitor is administered orally, wherein the PARP inhibitor is in a solution for oral administration.

In some embodiments, the combinations in the compositions, and the compositions for the kits, uses and/or methods described herein comprise, consist of, or consist essentially of, EGCG+PARP inhibitor, wherein EGCG is administered orally, wherein the amount of EGCG in a composition for oral administraiion is about 0.1 g to about 3 g, and wherein PARP inhibitor is administered orally, wherein the PARP inhibitor is in a composition for oral administration.

In some embodiments, the combinations in the compositions, and the compositions for the kits, uses and/or methods described herein comprise, consist of, or consist essentially of, quercetin+SPB+PARP inhibitor. In some embodiments, the combinations in the compositions, and the compositions for the kits, uses and/or methods described herein comprise, consist of, or consist essentially of, quercetin+EGCG+PARP inhibitor. In some embodiments, the combinations in the compositions, and the compositions for the kits, uses and/or methods described herein comprise, consist of, or consist essentially of, SPB+EGCG+PARP inhibitor. In some embodiments, the combinations in the compositions, and the compositions for the kits, uses and/or methods described herein comprise, consist of, or consist essentially of, quercetin+SPB+EGCG+PARP inhibitor.

The formulations of compositions and compositions for the kits, uses and/or methods described herein include but are not limited to the combinations provided in Table 4 below.

TABLE 4

Combinations for formulations of compositions and compositions for the kits, uses and/or methods described herein

| Combination | PARP inhibitor Oral | Quercetin | | | SPB | | | EGCG | | |
|---|---|---|---|---|---|---|---|---|---|---|
| | | IV; about 5 mg/ml to about 500 mg/ml | IV; about 0.05 g to about 10 g | Oral; about 100 mg to about 50 g | Liposomal; about 25 mg a day to about 100 mg a day | IV; about 20 mg/ml to about 2000 mg/ml | IV: about 0.5 g to about 100 g | Oral; about 0.1 g to about 50 g | IV: about 5 mg/ml to about 100 mg/ml | IV; about 0.01 g to about 15 g | Oral; about 0.1 g to about 3 g |
| 1. | X | | | | X | | | | | | |
| 2. | X | | | | | X | | | | | |
| 3. | X | | | | | | | | | | X |

TABLE 4-continued

Combinations for formulations of compositions and compositions for the kits, uses and/or methods described herein

| | | Quercetin | | | | SPB | | | EGCG | | |
|---|---|---|---|---|---|---|---|---|---|---|---|
| Combination | PARP inhibitor Oral | IV; about 5 mg/ml to about 500 mg/ml | IV; about 0.05 g to about 10 g | Oral; about 100 mg to about 50 g | Liposomal; about 25 mg a day to about 100 mg a day | about 20 mg/ml to about 2000 mg/ml | IV: about 0.5 g to about 100 g | Oral; about 0.1 g to about 50 g | IV: about 5 mg/ml to about 100 mg/ml | IV; about 0.01 g to about 15 g | Oral; about 0.1 g to about 3 g |
| 4. | X | | | | | | | | | | X |
| 5. | X | | | X | | | | X | | | |
| 6. | X | | | X | | | | | | | X |
| 7. | X | | | | | | | X | | | X |
| 8. | X | | | X | | | | X | | | X |
| 9. | X | | | | X | | | X | | | |
| 10. | X | | | | X | | | | | | X |
| 11. | X | | | | X | | | X | | | X |
| 12. | X | X | | | | | | | | | |
| 13. | X | | X | | | | | | | | |
| 14. | X | | | | X | | | | | | |
| 15. | X | | | | | X | | | | | |
| 16. | X | | | | | | X | | | | |
| 17. | X | | | | | | | | X | | |
| 18. | X | | | | | | | | | X | |
| 19. | X | X | | | | X | | | | | |
| 20. | X | X | | | | | | | X | | |
| 21. | X | | | | | X | | | X | | |
| 22. | X | X | | | | | X | | | | |
| 23. | X | X | | | | | | | | X | |
| 24. | X | | | | | | X | | | X | |
| 25. | X | | X | | | X | | | | | |
| 26. | X | | X | | | | | | X | | |
| 27. | X | | X | | | | X | | | | |
| 28. | X | | X | | | | | | | X | |
| 29. | X | | | X | X | | | | | | |
| 30. | X | | | X | | | | | X | | |
| 31. | X | | | X | | | X | | | | |
| 32. | X | | | X | | | | | | X | |
| 33. | X | X | | | | X | | | X | | |
| 34. | X | X | | | | X | | | | X | |
| 35. | X | X | | | | | X | | X | | |
| 36. | X | X | | | | | X | | | X | |
| 37. | X | | X | | | X | | | X | | |
| 38. | X | | X | | | X | | | | X | |
| 39. | X | | X | | | | X | | X | | |
| 40. | X | | X | | | | X | | | X | |

In Table 4, "X" indicates the components of the combinations for formulations of compositions and compositions for the kits, uses and/or methods described herein. Oral dosing of PARP inhibitor can be, but is not limited to, Rucaparib at 600 mg orally twice daily, Veriparib at 600 mg orally twice daily, Talazoparib at ≥0.5 mg orally once daily, Niraparib at 300 mg once daily, Olaparib at a recommended dose of 400 mg (8×50 mg capsules) taken orally twice daily (800 mg per day), Iniparib at 10 mg/kg to 70 mg/kg daily, and CEP 9722 at 150 mg a day. In some embodiments, including those in Table 4, in a combination comprising quercetin and SPB, the ratio of the concentration and/or dosing of quercetin and SPB ranges from about 1:2 to about 1:30. In some embodiments, including those in Table 4, in a combination comprising quercetin and SPB, the ratio of the concentration and/or dosing of quercetin and SPB is about 1:10. In some embodiments, including those in Table 4, in a combination comprising quercetin and SPB, the ratio of the concentration and/or dosing of quercetin and SPB is about 1:1.25, 1:1.5, 1:1.75, 1:2, 1:4, 1:6, 1:8, 1:10, 1:12, 1:14, 1:16, 1:18, 1:20, 1:22, 1:24, 1:26, 1:28, 1:30, 1:32, 1:34, 1:36, 1:38, 1:40, or a ratio within a range defined by any two of the aforementioned ratios.

In some embodiments, including but not limited to those in Table 4, the dose of quercetin ranges from about 0.5 g to about 2 g. In some embodiments, the dose of quercetin is about 0.1, 0.2, 0.3, 0.4, 0.5, 0.6, 0.7, 0.8, 0.9, 1 1.5, 2, 2.5, 3, 3.5, 4, 4.5, 5, 5.5, 6, 6.5, 7, 7.5, 8, 8.5, 9, 9.5 or 10 g, or within a range defined by any two of the aforementioned values. In some embodiments, the dose of SPB ranges from about 1 g to 15 g. In some embodiments, SPB is administered orally at a dose of about 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, or 75 g, or within a range defined by any two of the aforementioned values.

EXAMPLES

The following Examples are non-limiting. The cells lines, concentrations and doses of the anti-cancer agents and modulators disclosed in the following Examples are non-limiting. Other acceptable concentrations, ranges of concentrations, doses or ranges of doses are also contemplated.

Example 1

One or more patients are identified who have one or more cancers selected from lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, and breast cancer.

The one or more patients are administered a formulation comprising PARP inhibitor only. PARP inhibitor is given at various doses including Rucaparib at 600 mg orally twice daily, Veriparib at 600 mg orally twice daily, Talazoparib at ≥0.5 mg orally once daily, Niraparib at 300 mg once daily, Olaparib at a recommended dose of 400 mg (8×50 mg capsules) taken orally twice daily (800 mg per day), Iniparib at 10 mg/kg to 70 mg/kg daily, and CEP 9722 at 150 mg a day.

On the day of the next administration and prior to the administration, as assessment of the outcome of treatment until that point is conducted and compared to all previous assessments.

Assessment of the patients after an initial period of treatment in terms of parameters such as cancer progression, growth and size, indicates that the cancers have not progressed, slowed in growth, stopped growing/progressing, reduced in size, and/or eliminated. However, following the initial response period, patients show a decline in response to PARP inhibitor. The cancers eventually become resistant to PARP inhibitor. The cancers resume progressing and growing in size.

Patients are then administered a combination comprising a PARP inhibitor and at least one modulator selected from quercetin, SPB and EGCG as disclosed herein. PARP inhibitor is given at various doses including one or more of: Rucaparib at 600 mg orally twice daily, Veriparib at 600 mg orally twice daily, Talazoparib at ≥0.5 mg orally once daily, Niraparib at 300 mg once daily, Olaparib at a recommended dose of 400 mg (8×50 mg capsules) taken orally twice daily (800 mg per day), Iniparib at 10 mg/kg to 70 mg/kg daily, and CEP 9722 at 150 mg a day. The at least one modulator is given at a dose as disclosed herein. An assessment of the outcome of treatment is periodically made.

After a minimum period of treatment (e.g., one day), the patient shows improvement. Assessments of the cancer in terms of parameters such as its progression, growth and/or size, indicates that the cancer has not progressed, slowed in growth, stopped growing/progressing, remained the same or reduced in size, and/or been eliminated. Additional assessment shows that after therapy, patients have improved in one or more measures selected from the group of: Natural Killer cell activity, increased WBC count, decreased LDH activity, decreased tumor markers, shrinkage of tumor in radiographic studies, decrease in CRP (correlation with improved survival), improved IgF-1. In some cases, the patients do not show a decline in response to the combination comprising a PARP inhibitor+at least one modulator selected from quercetin, SPB and EGCG as disclosed herein during the course of the treatment, and the cancers are eventually eliminated without relapse.

Example 2

One or more patients are identified who have one or more cancers selected from lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, and breast cancer.

Patients are then administered a combination of PARP inhibitor and at least one modulator selected from quercetin, SPB and EGCG as disclosed herein. PARP inhibitor is given at various doses including one or more of: Rucaparib at 600 mg orally twice daily, Veriparib at 600 mg orally twice daily, Talazoparib at ≥0.5 mg orally once daily, Niraparib at 300 mg once daily, Olaparib at a recommended dose of 400 mg (8×50 mg capsules) taken orally twice daily (800 mg per day), Iniparib at 10 mg/kg to 70 mg/kg daily, and CEP 9722 at 150 mg a day. The at least one modulator is given at a dose as disclosed herein. An assessment of the outcome of treatment is periodically made.

After a minimum period of treatment (e.g., one day), the patient shows improvement. Assessments of the cancer in terms of parameters such as its progression, growth and/or size, indicates that the cancer has not progressed, slowed in growth, stopped growing/progressing, remained the same or reduced in size, and/or been eliminated. Additional assessment shows that after therapy, patients have improved in one or more measures selected from the group of: Natural Killer cell activity, increased WBC count, decreased LDH activity, decreased tumor markers, shrinkage of tumor in radiographic studies, decrease in CRP (correlation with improved survival), improved IgF-1. In some cases, the patients do not show a decline in response to the combination of PARP inhibitor+at least one modulator selected from quercetin, SPB and EGCG as disclosed herein during the course of the treatment, and the cancers are eventually eliminated without relapse.

Example 3—Guardant360 Tumor Response Map & Somatic Alteration Burden

The Guardant360 Tumor Response Map (FIG. 1, FIG. 7, FIG. 16 and FIG. 18) illustrates the relative changes of observed in cell-free DNA (cfDNA) at different sample submission time points. The "Somatic Alteration Burden" value in the Guardant360 Tumor Response Map refers to the maximum % cfDNA detected at each time point. Amplifications are not plotted, and only the first and last four test dates are plotted. The percentage, or allele frequency, of altered % cfDNA circulating in blood is related to the unique tumor biology of each patient (FIG. 2-FIG. 5, FIG. 8, FIG. 9, FIG. 17, FIG. 19). Factors that may affect the % cfDNA of detected somatic alterations (e.g., deletion, mutation, amplification, or a combination thereof) include tumor growth, turn-over, size, heterogeneity, vascularization, disease progression, and treatment. The genes covered by the Guardant360 Tumor Response Map are listed in Table 5.

TABLE 5

Genes detected by Guardant360 Tumor Response Map
Complete Sequencing of Covered Exons*

| Point Mutations (SNVs) (73 Genes) | | | | | | | Indels (23 Genes) | | Amplifications (CNVs) (18 Genes) | | Fusions (6 Genes) |
|---|---|---|---|---|---|---|---|---|---|---|---|
| AKT1 | ALK | APC | AR | ARAF | ARID1A | ATM | ATM | APC | AR | BRAF | ALK |
| BRAF | BRCA1 | BRCA2 | CCND1 | CCND2 | CCNE1 | CDH1 | ARID1A | BRCA1 | CCND1 | CCND2 | FGFR2 |
| CDK4 | CDK6 | CDKN2A | CTNNB1 | DDR2 | EGFR | ERBB2 | BRCA2 | CDH1 | CCNE1 | CDK4 | FGFR3 |
| ESR1 | EZH2 | FBXWI | FGER1 | FGFR2 | FGFR3 | GATA3 | CDKN2A | EGFR | CDK6 | EGFR | NTRK1 |
| GNA11 | GNAQ | GNAS | HNF1A | HRAS | IDH1 | IDH2 | ERBB2 | GATA3 | ERBB2 | FGFR1 | RET |
| JAK2 | JAK3 | KIT | KRAS | MAP2K1 | MAP2K2 | MAPK1 | KIT | MET | FGFR2 | KIT | ROS1 |
| MAPK3 | MET | MLH1 | MPL | MTOR | MYC | NF1 | MLH1 | MTOR | KRAS | MET | |
| NFE2L2 | NOTCH/ | NPM1 | NRAS | NTRK1 | NTRK3 | PDGFRA | NF1 | PDGERA | MYC | PDGFRA | |
| PIK3CA | PTEN | PTPN11 | RAFI | RBI | RET | RHEB | PTEN | RB1 | PIK3CA | RAF1 | |
| RHOA | RIT1 | ROSI | SMAD4 | SMO | STK11 | TERI** | SMAD4 | STK11 | | | |
| TP53 | TSC1 | VHL | | | | | TP53 | TSC1 | | | |
| | | | | | | | VHL | | | | |

**includes TERT promoter region
*Exons selected to maximize detection of known somatic mutations. List available upon request.

Results related to cfDNA (FIG. 2-FIG. 5, FIG. 8, FIG. 9, FIG. 17, FIG. 19) are categorized as follows: ND represents genomic alterations not detected. Genomic alterations may be present that are below the limit of detection of this test. Certain sample or variant characteristics may result in reduced analytic sensitivity, such as poor sample quality or improper collection. Genomic alterations in a tumor may be present but are not detected in circulating cell-free DNA from this blood specimen with this test. ≠ refers to synonymous mutations and Variants of Uncertain Significance (VUSs). The functional consequences and clinical significance of this gene variant are not established. Similar to other alterations in circulating cfDNA, the amount (% cfDNA) of this variant may reflect disease progression or response to treatment. Therefore, clinical correlation is advised. AMP represents gene amplification results in increased copies of the gene present in the cfDNA. As the absolute number of copies in circulation is dependent on both tumor fraction and the magnitude of the tumor amplification, amplifications are reported on a semi-quantitative scale. Positive (+) refers to amplification magnitude is in the lower $50^{th}$ percentile of samples with amplifications; Strongly Positive (++) refers to amplification magnitude is in the 50th to 90th percentile; Very Strongly Positive (+++) refers to amplification magnitude is in the top 10th percentile. Guardant360 detects amplifications in the genes listed in Table 5.

Prior to the initiation of treatment, somatic alterations were detected in the circulating cell-free DNA isolated from this patient's blood specimen. These genomic alterations are cancer-associated somatic variants, some of which have been associated with either increased or reduced clinical response to specific treatments. Amplification was detected in the circulating cell-free DNA isolated from this patient's blood specimen for the annotated gene(s). Unlike tissue-based gene amplification tests (e.g., IHC or FISH), Guardant360 assesses the total representation of a given gene in all circulating cell-free DNA present in the patient's blood sample including material derived from the tumor and healthy tissue alike. As such, the absolute level of amplification present in the blood depends both on the tumor-derived cfDNA content and on the degree of amplification within that fraction and cannot be inferred from bulk cfDNA interrogation. For example, a positive Guardant360 test could represent a small population of cells with extremely high levels of the detected gene amplification. Alternatively, it could represent a large population of cells with low to medium levels of the detected gene amplifications. The exact correlation between amplification detected by Guardant360 compared to IHC or FISH and how each test differentially guides patient management is an area of active investigation.

Example 4—Case Study 1 (Biological Modulation of PARP Inhibition in Triple Negative Breast Cancer)

Provide herein is a discussion of a case study of a patient with stage four refractory and resistant BRCA1 mutated triple negative breast cancer who responded in two weeks to a combinational therapy consisting of PARP inhibitor and quercetin (administered as quercetin PG) and SPB. As the patient already had exhausted the PARP inhibitor by excessive presence of BRCA positive altered circulating DNA, the response essentially reflects the quercetin and SPB therapy as the back bone of treatment. The liquid biopsy repeated after two weeks of combination therapy showed complete disappearance (resolution of positive BRCA gene/circulating DNA), reflecting a synergism by proposed modulation of resistance as mechanism of action. The initial circulating DNA showed 93% mutation allele fraction (MAF) of BRCA gene. This is believed to be the first study on the disclosed combinational therapy in human. By providing a superior treatment to current standards, the finding in this study could potentially change the standard of care in treating BRCA positive tumors.

The patient was a 37-year-old female with breast carcinoma with metastasis to bone, lymph nodes and brain. The patient was initially diagnosed with stage III right breast carcinoma and 4 axilla lymph nodes. The carcinoma was positive for BRCA1 mutation with metastases and was estrogen receptor positive. The patient received four cycles of Adriamycin/Taxol/Cytoxan (ACT) as follows: Day 1: Doxorubicin 60 mg/m$^2$ IV Day 1: Cyclophosphamide 600 mg/m$^2$ IV. Repeat cycle of Doxorubicin and Cyclophosphamide every 21 days for 4 cycles, followed by: Day 1: Paclitaxel 80 mg/m$^2$ by 1-hour IV infusion weekly for 12 weeks. Thereafter, the patient underwent double mastectomy, followed by 36 rounds of radiation therapy on daily basis, and then prophylactic oophorectomy.

Twenty three months from her initial diagnosis, her CA 27-29 marker was noted to be elevated and scans indicated metastases to left lung and left clavicle lymph nodes. The patient participated in a UCLA trial with PARP inhibitor Talazoparib at >0.5 mg orally once daily over the next four months. Patient then switched to Xeloda for the next three months. The patient was on Aromatase inhibitor and Ibrance for the next two months. The patient received Carbo/Gemzar for the next two months but during this time period patient developed pain in sacrum. For the next one month, the patient received radiation to sacrum with relief of pain and also received radiation to two brain lesions per cyberknife. For the next two months, the patient participated in a Stanford trial (BMO1103) and received more radiation to another brain lesion. The patient also received 10 rounds on daily basis of radiation to lesions noted on neck.

Figure 6:
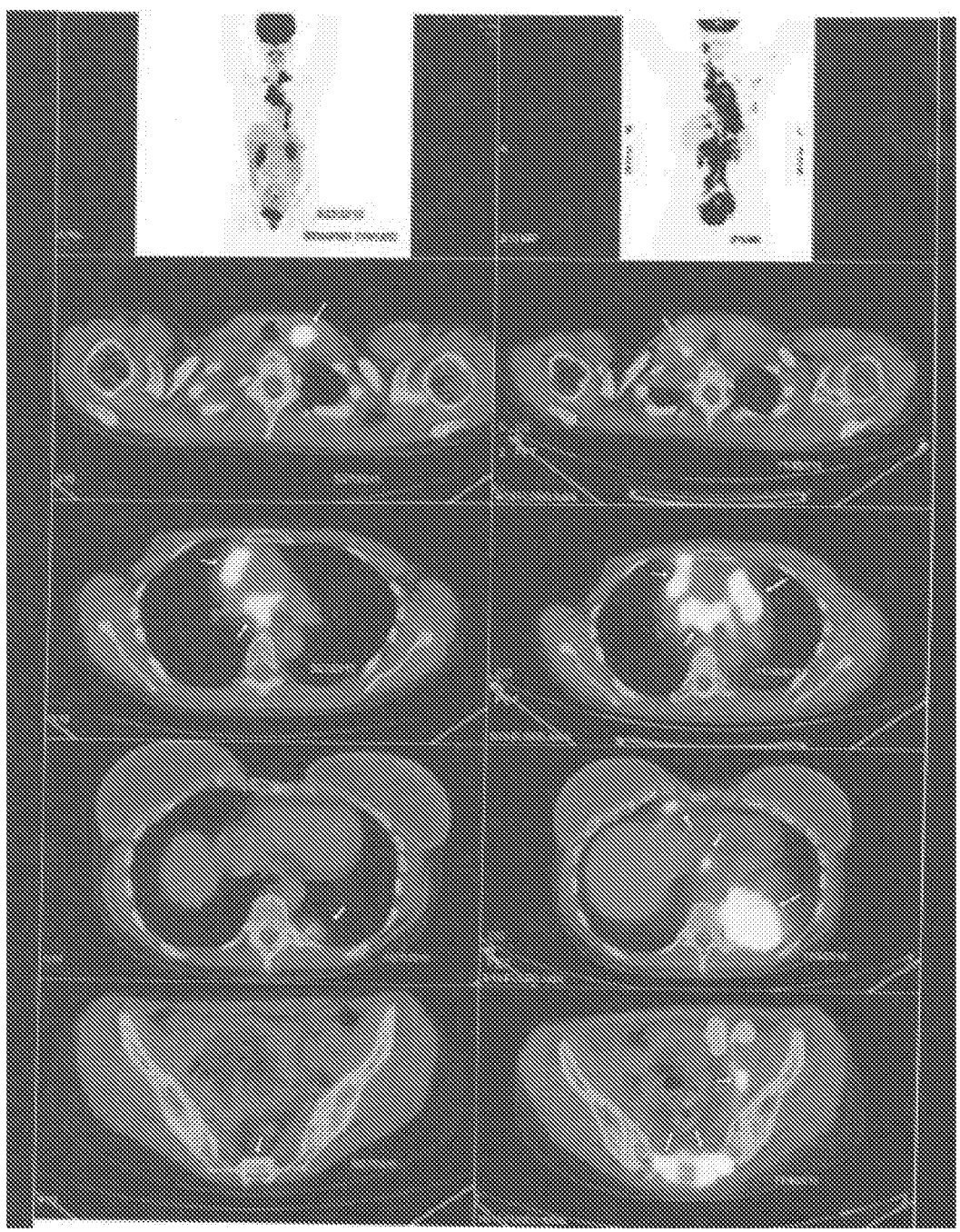
FIG. 6 shows PET scans from before (left panel) and after (right panel) treatment.
Figure 7:
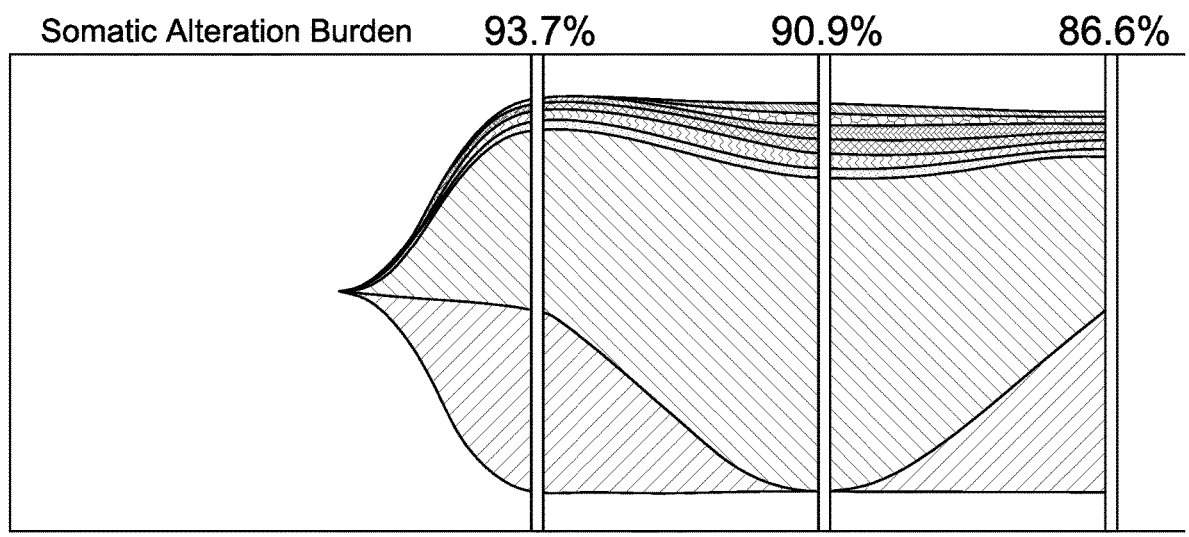
FIG. 7 shows an embodiment of a Guardant360 Tumor Response Map from Test Number 3 (see, Example 4).

After a duration of about one month, the patient started immunotherapy with Keytruda at a dose of 100 mg/4 ml injection monthly (25 mg/ml), PARP inhibitor Olaparib at 800 mg per day, and Amiridex at 1 mg per day. At the time of starting treatment, a comparison of her restaging PET scan to her PET from 18 months earlier showed very large mass in the left lower lung, as well as severe lymphadenopathies in her neck, thorax and pelvis, retroperitoneum with mass effect on IVC, causing hydronephrosis and partial colon obstruction, due to peritoneal carcinomatosis, along with sacrum large lesion with significant uptake (FIG. 6).

She was then referred by her oncologist to Dr. Nezami for evaluation and treatment. On her initial evaluation, she was in significant pain. Laboratory analysis indicated 93% MAF of circulating DNA with several alterations, including BRCA. Circulating tumor cells (CTCs) were positive for three out of four markers, at extensively high levels.

The patient was immediately started on daily IV therapy and PARP inhibitor Olaparib at 800 mg per day in conjunction with EGCG (Green Tea extract) at 1 g IV daily and quercetin PG at 0.5 g IV daily. After starting the treatments, she started feeling better and breathing better and more sense of well-being after the first two treatments. Her pain was significantly better, she felt less nauseous and had more appetite.

At the start of her treatment, molecular profiling of circulating tumor cells (CTCs) was performed as follows. In order to obtain CTCs from the patient's peripheral blood, large cells and cell-clusters as well as epithelial cells were isolated. A preparation of mononuclear cells (MNC) served as a control cell fraction. mRNA was isolated from all fractions. Thereafter, the expression of tumor relevant genes was measured by quantitative real-time RT-PCR. A preparation of mononuclear cells (MNC) served as a control cell fraction. The expression of the telomerase gene can be increased in most tumor types but not in normal tissue. An increased expression of telomerase gene may be indicative of the presence of tumor cells in the circulation. Overexpression of telomerase was detected in the isolated cells. The detection of expression of cytokeratin (CK) 19 indicates the presence of epithelial cells and may thus be indicative for circulating tumor cells. Strong expression of CK19 was detected. Overexpression of C-MYC indicates an increased proliferation of the isolated cells. An increased proliferation rate is a typical feature of tumor cells. The expression of level of C-MYC was elevated. Overexpression of ERBB2 (HER2/NEU) is a trait of different types of cancer and may also be observed in breast cancer. Thus, the detection of ERB B2 overexpression may be indicative of the presence of circulating tumor cells. The expression of ERBB2 was elevated. Thus, in the isolated tumor cell fraction, expression of ERBB2, C-MYC and telomerase was above threshold (>2.0) and expression of CK19 was above threshold (>0) in the very high range (>10000). These findings were likely indicative of the presence of CTCs in the analyzed blood sample.

After two weeks of treatment with PARP inhibitor Olaparib at 800 mg per day in conjunction with EGCG at 1 g IV daily and quercetin at 0.5 g IV daily, her laboratory analysis results showed significant improvements. There was a reduction in her tumor markers (CA-27.29 and CA-15.3) and LDH. Her CA-15.3 has decreased from 249 to 179 and LDH had decreased from 1603 to 1348 and went further down to 1298 after another two weeks. Also, after the initial two weeks of therapy, all her CTC markers dropped including the CK19 (from 47735 to 18818), telomerase (49.6 to 19.1), ERBB2 (27.8 to 12.35) and C-MYC (5.65 to 3.15). This decrease occurred without any additional chemotherapy. Thus, the measured values of the detection markers suggested that the tumor cell burden in blood had decreased compared to the analysis at the start of treatment. However, the markers were still elevated and in the higher range.

Figure 2:
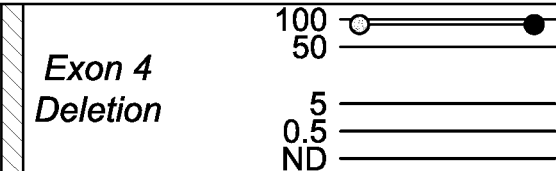
FIG. 2 shows a summary of somatic alterations from Test Number 2.
Figure 3:
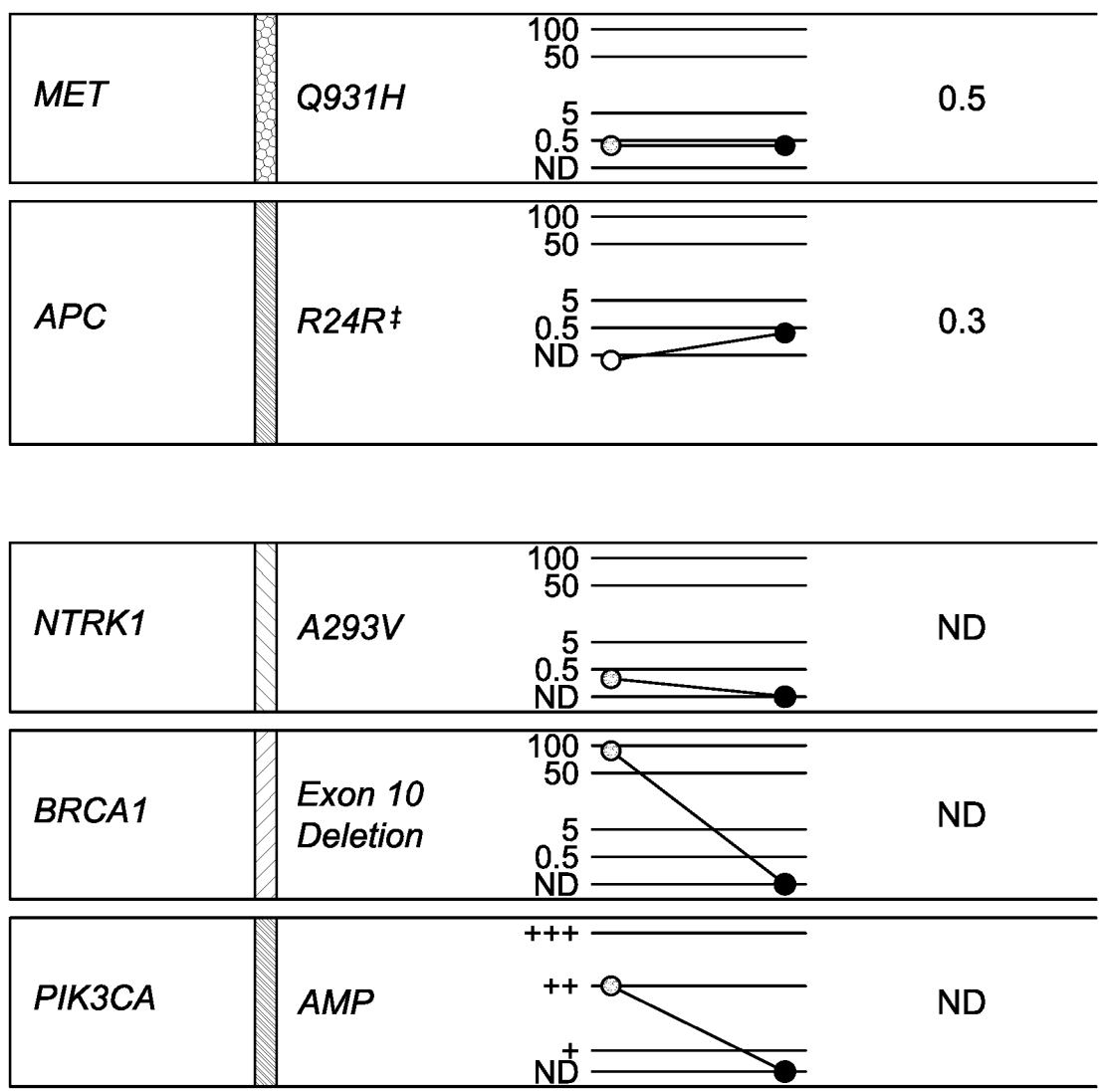
FIG. 3 shows a summary of somatic alterations from Test Number 2.
Figure 4:
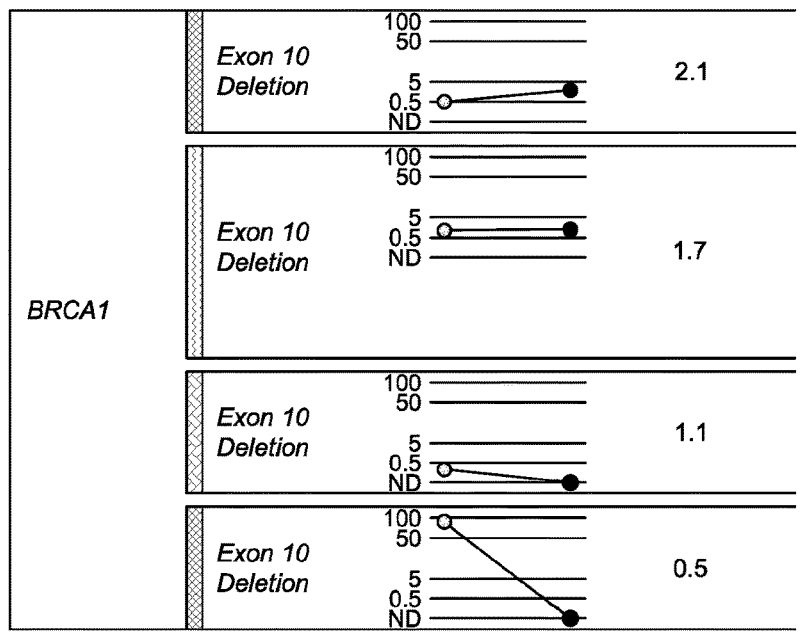
FIG. 4 shows a summary of somatic alterations and associated treatment options from Test Number 2.
Figure 4:
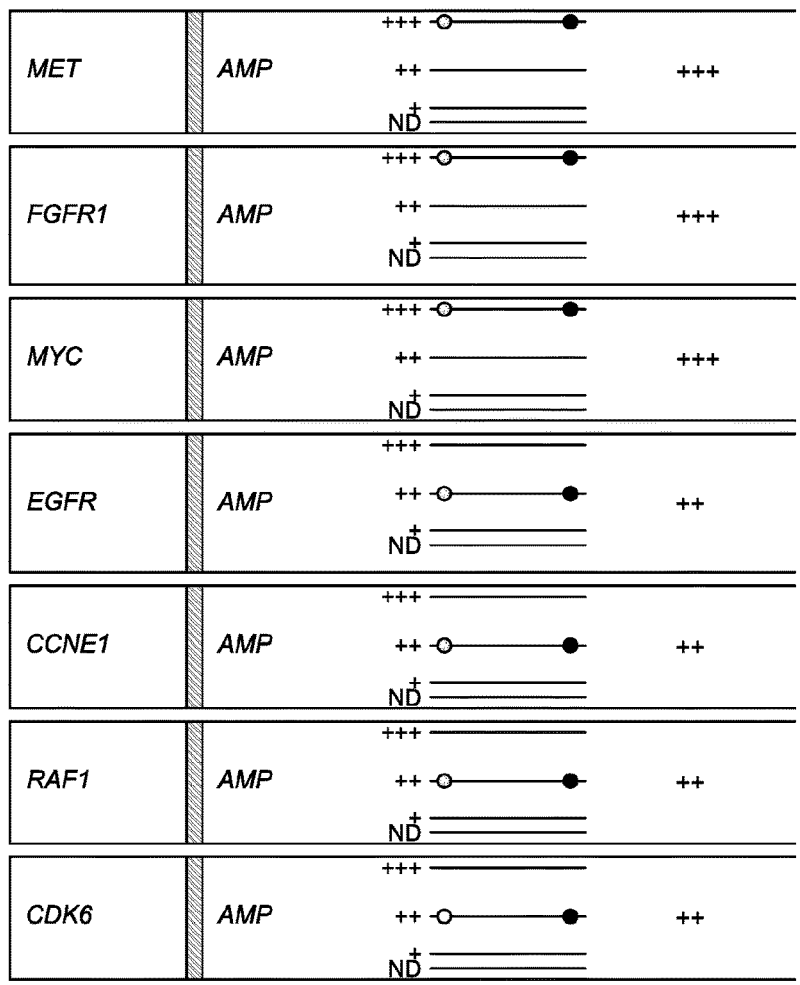
Figure 5:
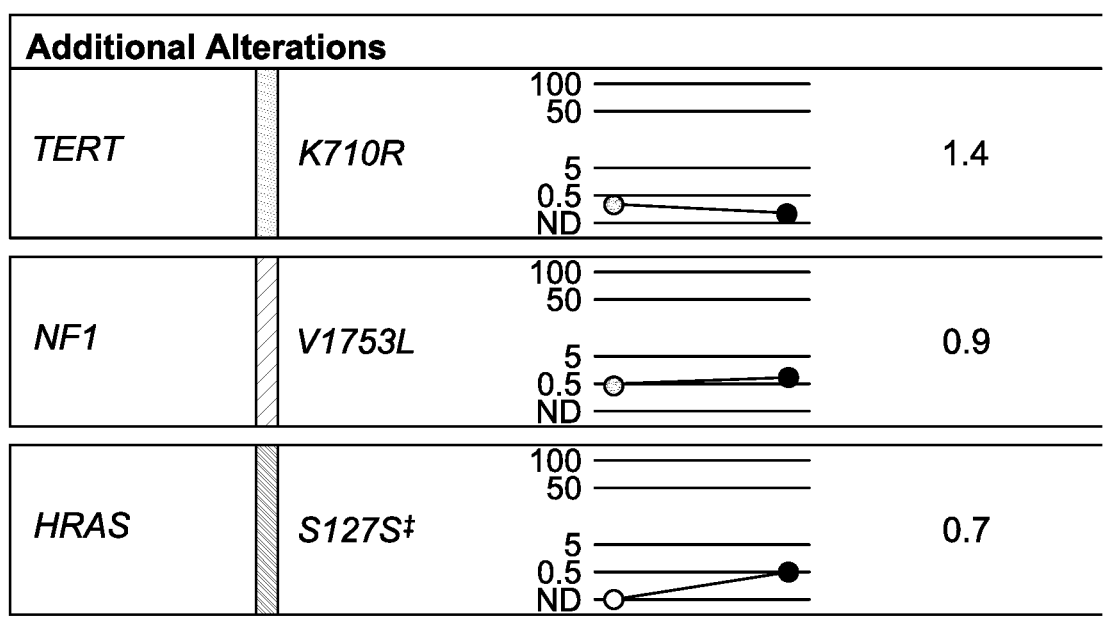
FIG. 5 shows a summary of somatic alterations from Test Number 2.
Figure 8:
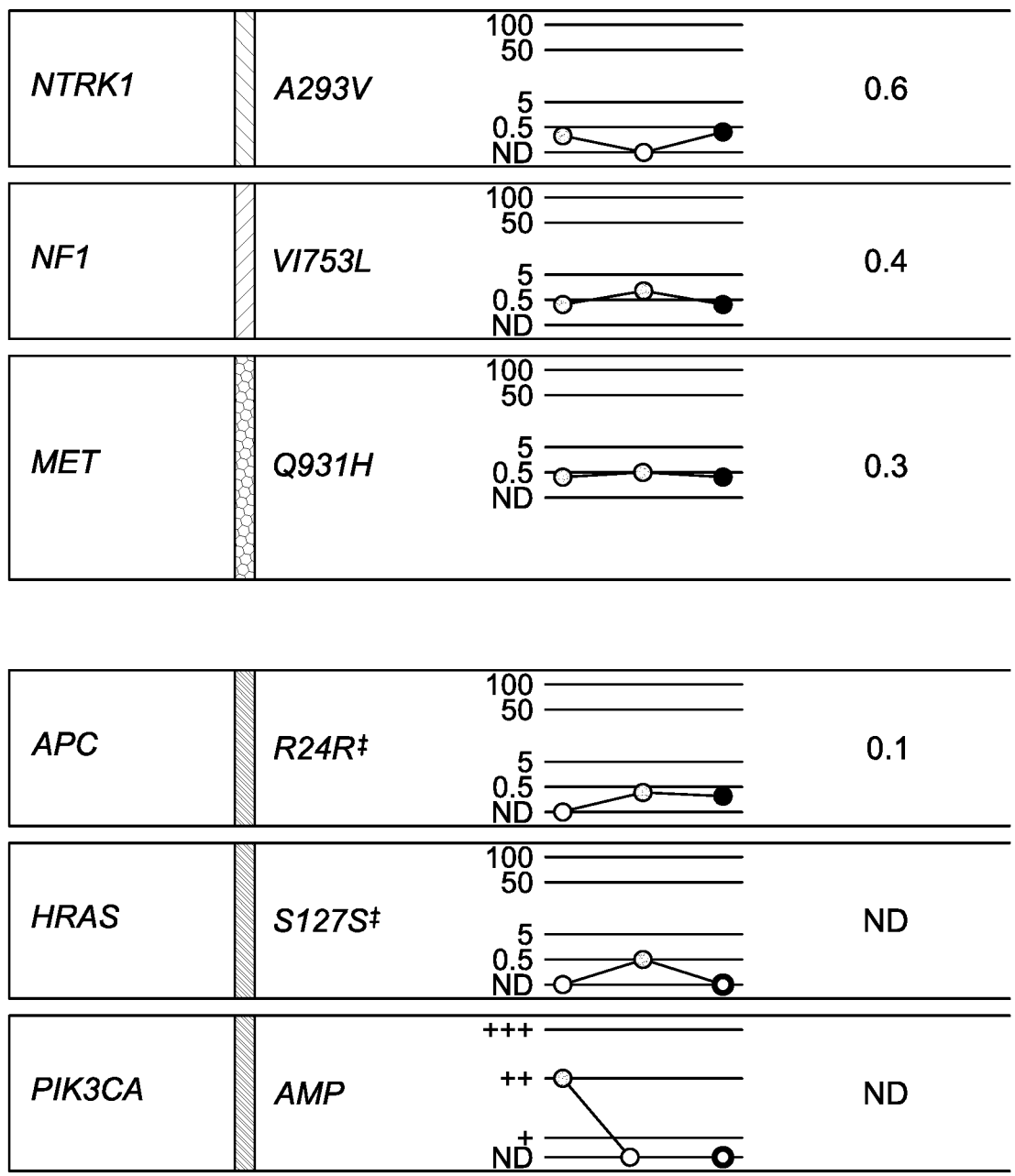
FIG. 8 shows a summary of somatic alterations from Test Number 3.
Figure 9:
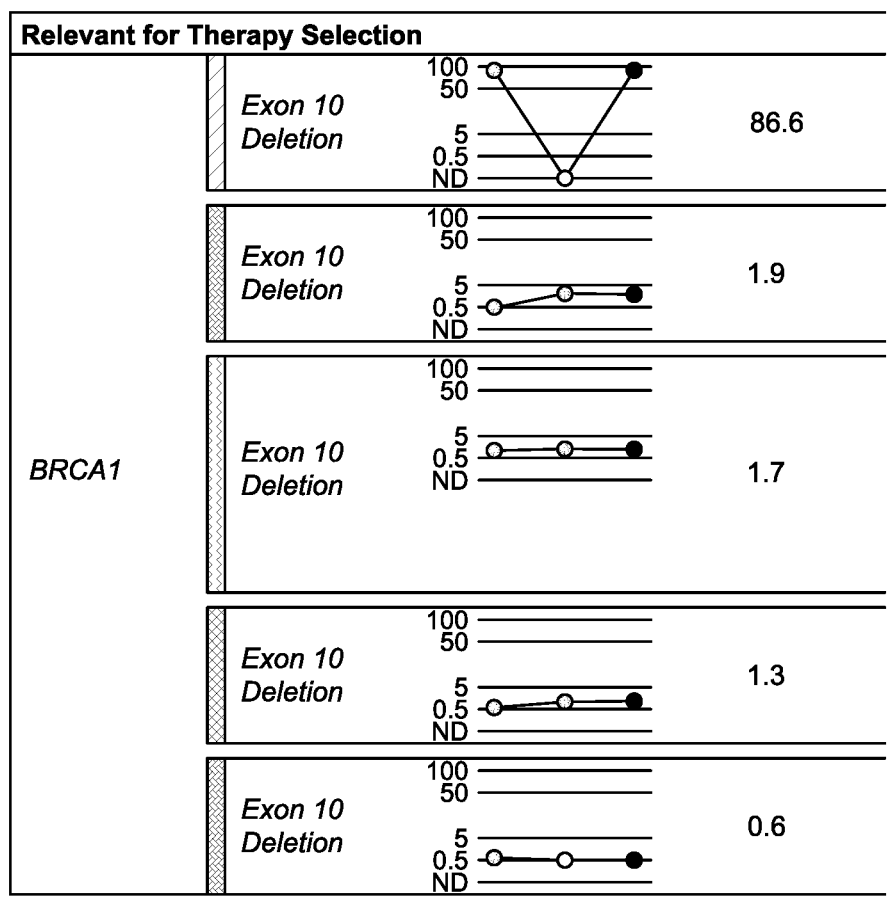
FIG. 9 shows a summary of somatic alterations and associated treatment options from Test Number 3.
Figure 9:
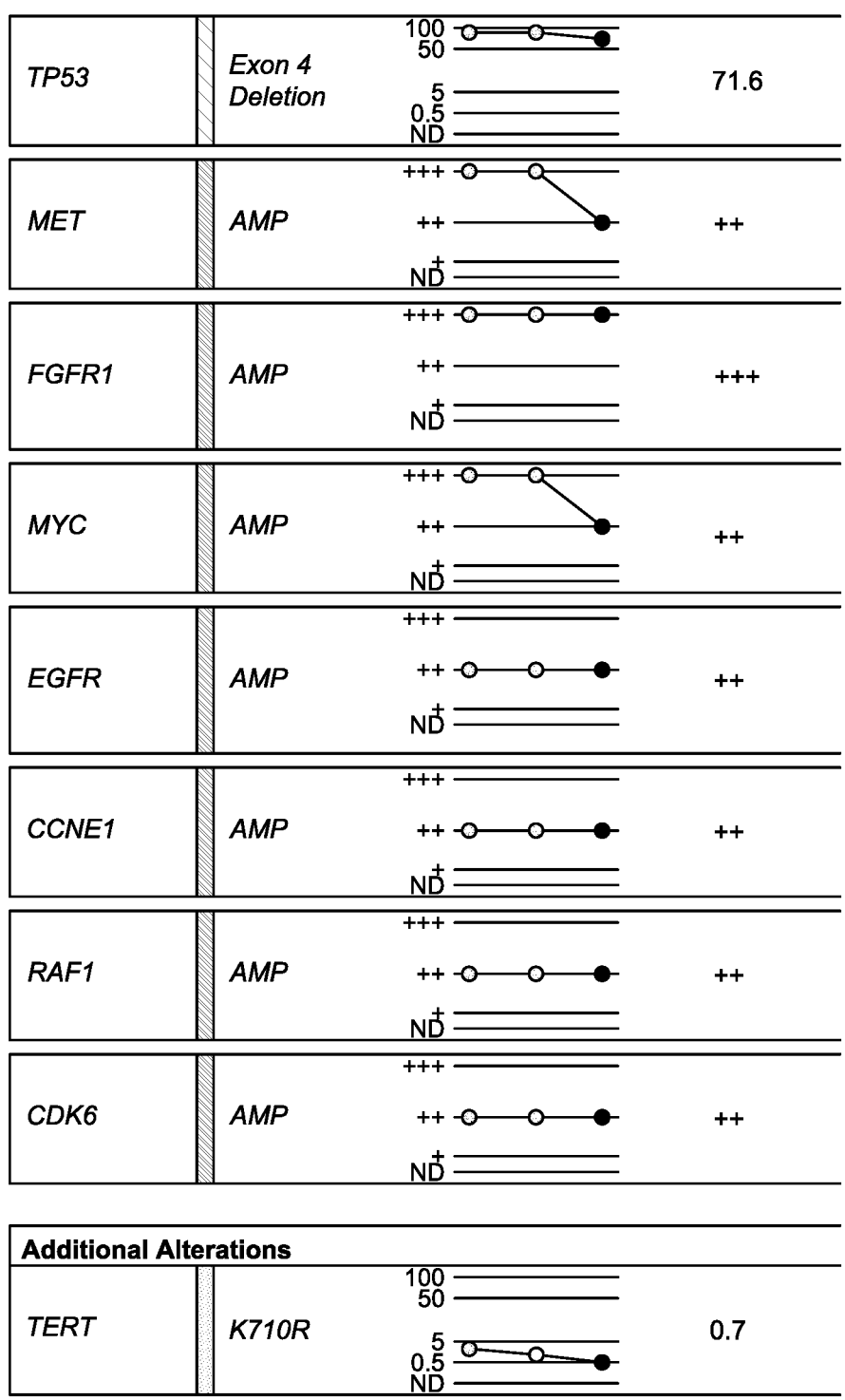

Before the initiation of treatment with the combination of PARP inhibitor, and EGCG and quercetin described earlier, the following alterations (deletions) were detected in this patient: TP53 Y103fs (FIG. 2); BRCA1 L666fs, R664fs, K690fs, S681fs (FIG. 3). Guardant360 detects short deletions in exons of certain genes (Table 5), including potential splice site-disrupting events. After the initial two weeks of treatment with a combination of PARP inhibitor and EGCG and quercetin, PARP inhibitor therapy was discontinued and the patient was only administered EGCG and quercetin. A repeat analysis performed four weeks later showed increased BRCA back up again at 86% (compare FIG. 1 with FIG. 7) and the following alterations (deletions) were detected in this patient: TP53 Y103fs; BRCA1 L666fs, R664fs, K690fs, S681fs, K654fs (FIG. 8 and FIG. 9). Guardant360 detects short deletions in exons of certain genes (Table 5), including potential splice site-disrupting events.

The re-appearance of BRCA mutated cells in the liquid biopsy after four weeks of treatment with quercetin and EGCG only (without PARP inhibitor) confirmed that the combination quercetin and EGCG only (without PARP inhibitor) was less effective by itself. However, the combination of quercetin and EGCG was able to modify the response to PARP inhibitor, which by itself had initially failed, indicating the improved efficacy of the disclosed combination therapy in comparison to the PARP inhibitor alone, or the quercetin PG and EGCG alone.

Figure 10:
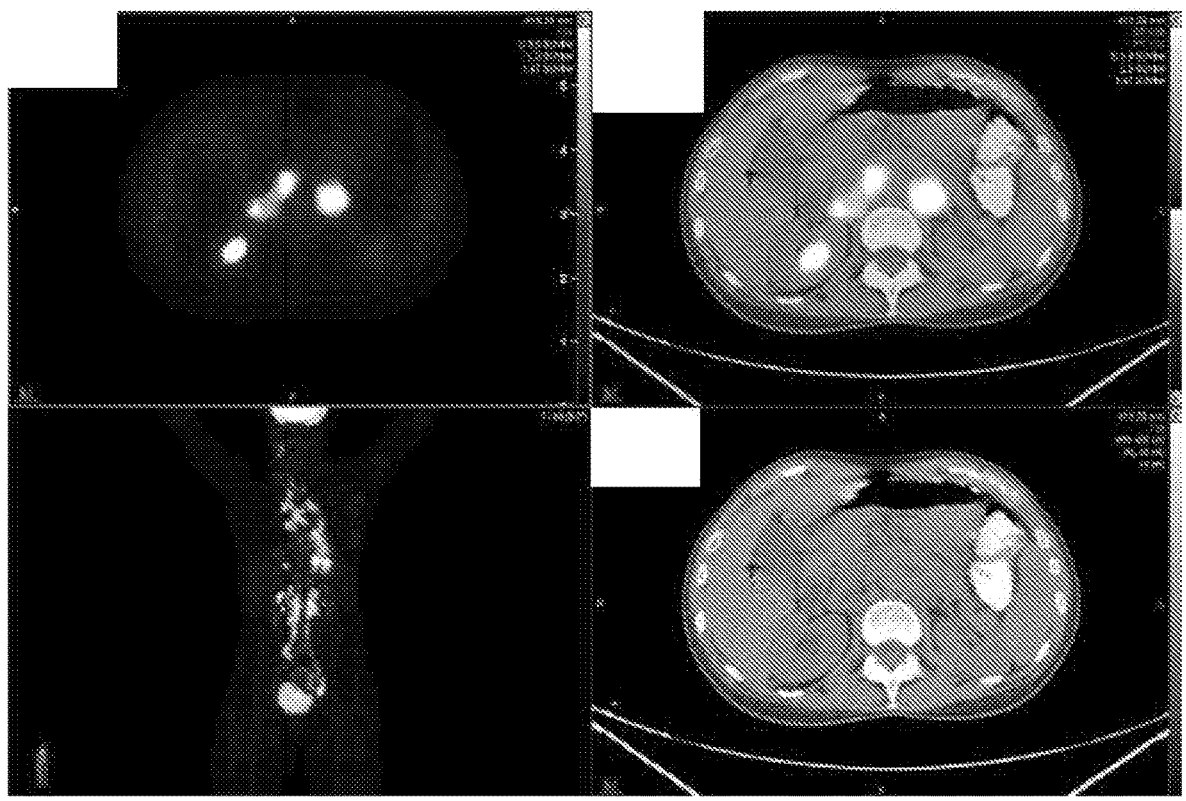
FIG. 10 shows a PET/CT scan of a patient (see, Example 4).
Figure 11:
FIG. 11 shows a PET/CT scan of a patient (see, Example 4).
Figure 12:
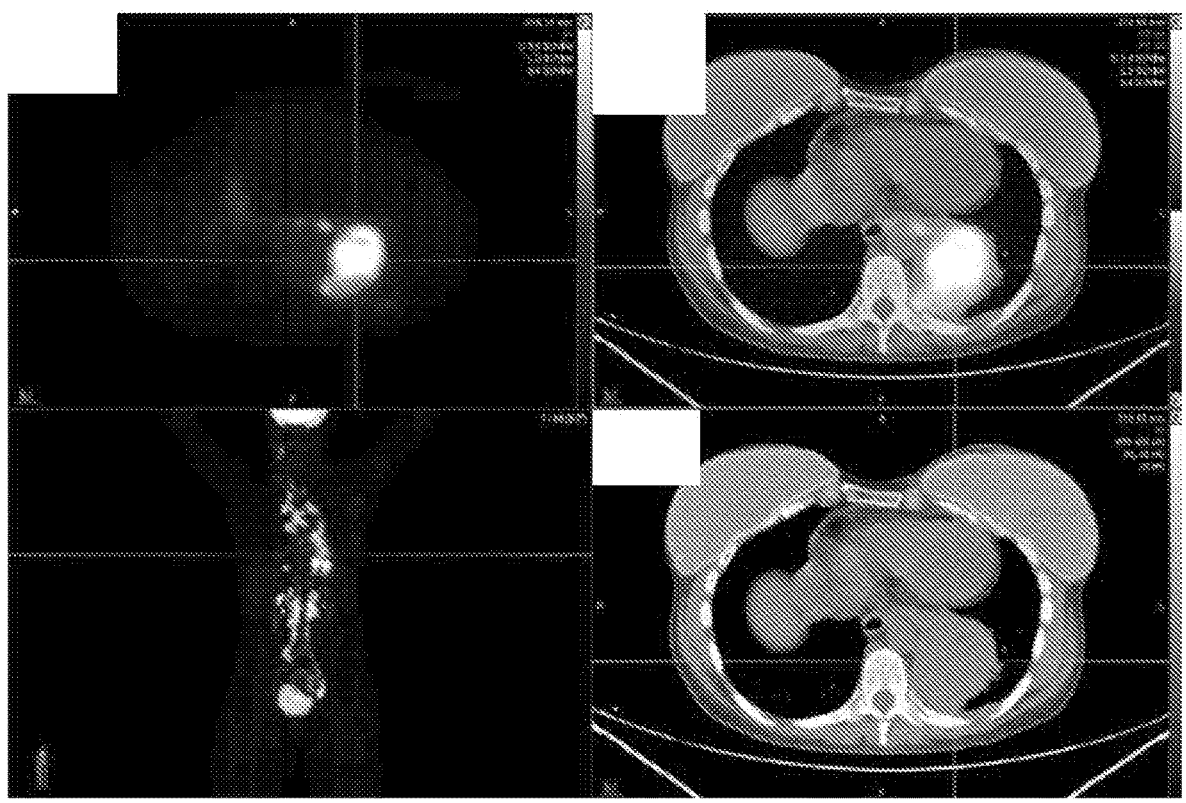
FIG. 12 shows a PET/CT scan of a patient (see, Example 4).
Figure 13:
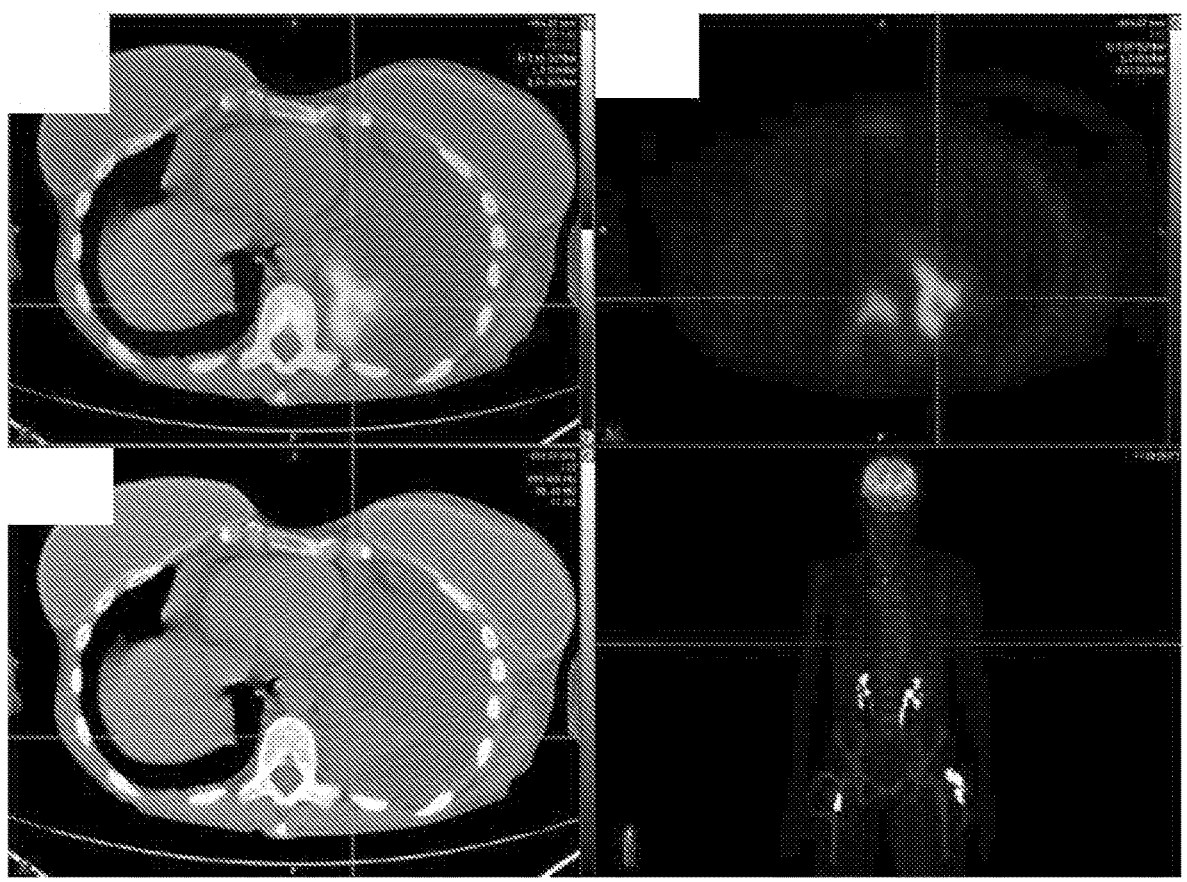
FIG. 13 shows a PET/CT scan of a patient (see, Example 4).
Figure 14:
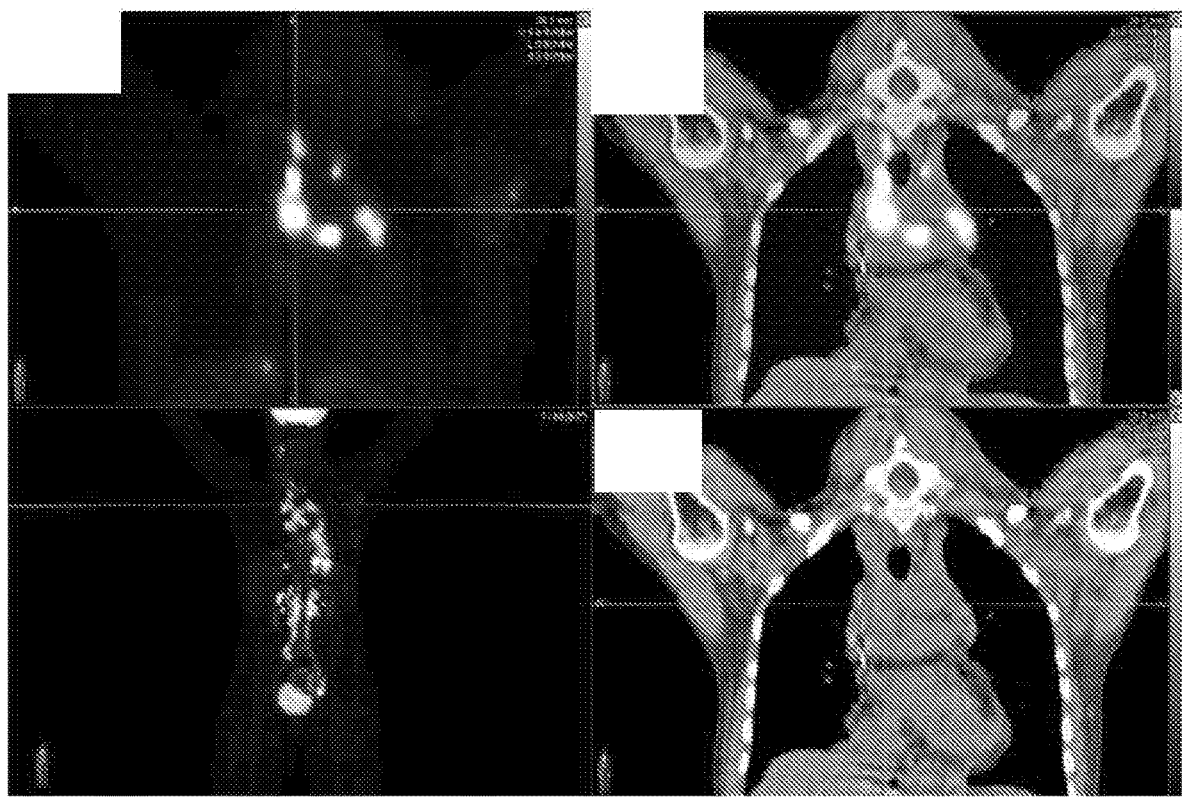
FIG. 14 shows a PET/CT scan of a patient (see, Example 4).
Figure 15:
FIG. 15 shows a PET/CT scan of a patient (see, Example 4).
Figure 16:
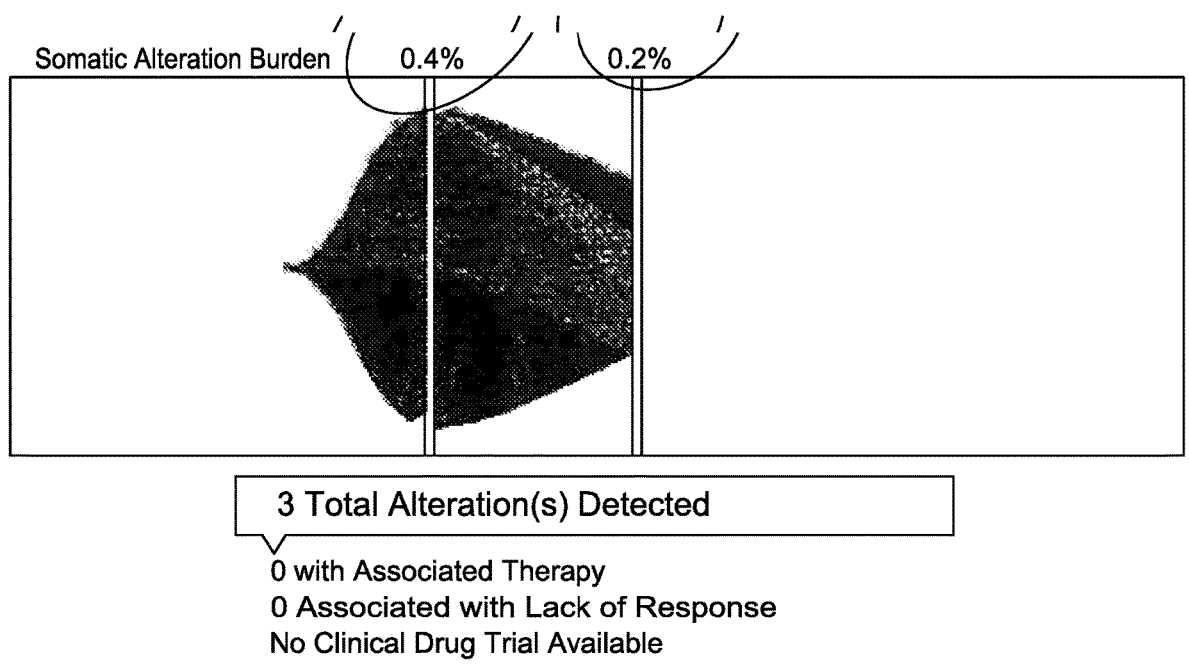
FIG. 16 shows an embodiment of a Guardant360 Tumor Response Map (see, Example 5).

At this point, the patient was re-administered a combination of PARP inhibitor Olaparib at 800 mg per day and quercetin (administered as quercetin PG) at 0.5 g IV daily and EGCG at 1 g IV daily. Thereafter, her CT and PET scans were repeated. A comparison (FIG. 10, FIG. 12 and FIG. 14 with FIG. 11, FIG. 13 and FIG. 15, respectively) of her CT and PET scans from before the initiation of treatment with the combination of PARP inhibitor and quercetin and EGCG and three months later (i.e., after about six weeks of re-administering a combination of PARP inhibitor and quercetin and EGCG) showed significant reduction in sizes and burden of her cancers.

In summary, application of the disclosed combination therapy comprising PARP inhibitors and quercetin and EGCG is feasible and clinically relevant. Such therapy showed significant effectiveness in treating BRCA positive colonies in tumor in triple negative breast cancer. The correlation of liquid biopsy findings and clinical response to such combinational therapy is also important as it can be used as a companion diagnostic for the therapy. It is believed that such therapy could replace the current standard of care in advanced triple negative breast cancer harboring BRCA deficient somatic or germ line mutations.

Example 5—Case Study 2

This is a case study of a 48-year-old female with history of high grade stage HIC serous ovarian carcinoma, status post laparoscopic surgery. She had undergone radical Total Abdominal Hysterectomy with Bilateral Salpingo-Oophorectomy (TAHBSO), omentectomy and right diaphragm stripping, and resection of 7 cm mass in left ovary, involving rectosigmoid and mesentery, a total of 6/23 lymph nodes (LNs) were involved, status post dose dense systemic taxol and carboplatinum for six cycles for about four months. She was not a candidate for IP chemotherapy, with severe side effects (neuropathy) and further progressive disease evident on scan. Therefore, the patient was switched to Carbo and Doxil, as after only one cycle she complained of brain fog, neuropathy, and sleep apnea, as well as episodes of asthma. She was referred to the clinic of Dr. Nezami to be evaluated for epigenetic therapies.

A CT scan was performed which showed scattered metastatic implants within the abdomen and pelvis, left periaortic lymphadenopathy, enlarging mesenteric LN, left axillary LN, and left adrenal gland implant which was reported as new finding along with anterior mediastinum soft tissue.

Upon evaluation, her BRCA testing was positive for BRCA1 mutation. She had previously been evaluated by her oncologist at a different medical facility. Her CA 125 had been increasing. She also had diarrhea.

After initiation of treatment at the clinic of Dr. Nezami, her diarrhea stopped. As she was experiencing some neuropathy in her face, she asked for her chemotherapy to be put on hold. However, she was recommended to continue the current regimen at adjusted dose due to side effects.

At the start of her treatment, molecular profiling of circulating tumor cells (CTCs) was performed as follows. In order to obtain CTCs from the patient's peripheral blood, large cells and cell-clusters as well as epithelial cells were isolated. A preparation of mononuclear cells (MNC) served as a control cell fraction. mRNA was isolated from all fractions. Thereafter, the expression of tumor relevant genes was measured by quantitative real-time RT-PCR. A preparation of mononuclear cells (MNC) served as a control cell fraction. The expression of the telomerase gene can be increased in most tumor types but not in normal tissue. An increased expression of telomerase gene may be indicative of the presence of tumor cells in the circulation. Overexpression of telomerase was detected in the isolated cells. The detection of expression of cytokeratin (CK) 20 indicates the presence of epithelial cells and may thus be indicative for circulating tumor cells. There was no expression of CK20 detected. Overexpression of C-MYC indicates an increased proliferation of the isolated cells. An increased proliferation rate is a typical feature of tumor cells. The expression of level of C-MYC was not elevated. Overexpression of ERBB2 (HER2/NEU) is a trait of different types of cancer and may also be observed in breast cancer. Thus, the detection of ERBB2 overexpression may be indicative of the presence of circulating tumor cells. The expression of ERBB2 was elevated. Thus, in the isolated tumor cell fraction, expression of telomerase and ERBB2 was above threshold (>2.0). These findings were likely indicative of the presence of CTCs in the analyzed blood sample. Her laboratory tests showed VEGF at 118. CA 125, and LDH, and CTCs were positive for ERBB2 and telomerase. Molecular profiling of cfDNA showed mutations in SMO, ROS1, P53, PTEN and BRCA1, as well as estrogen receptor (ER) at 90 percent.

She was immediately started on IV epigenetic therapies which she received on daily basis for two weeks. Her treatments consisted of Niraparib and IV epigenetic therapies, consisting of quercetin (administered as quercetin) PG and SPB. Her laboratory tests were repeated after two weeks, which showed significant reduction in her VEGF (decreased from 118 to 52). Her CA 125 had decreased from 140 to 49.7. Her CA 125 assay was repeated about one month later and it was at 17.9 (i.e., normal range).

Figure 17:
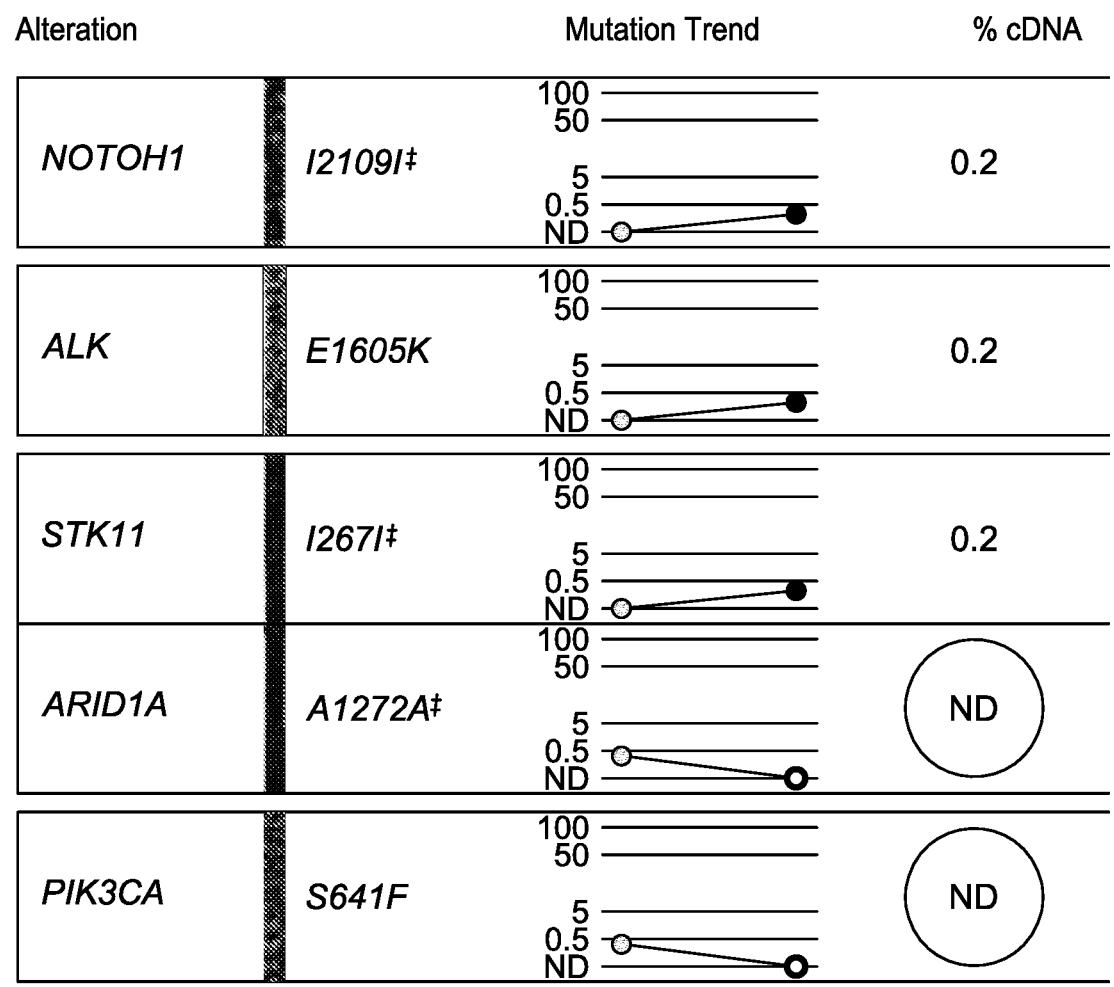
FIG. 17 shows a summary of somatic alterations from Example 5.

Her cfDNA showed improvement in mutated allele frequency (MAF) which decreased from 0.4 percent at the start of treatment to 0.2% for NOTOH1, ALK and STK11 (FIG. 16 and FIG. 17), and non-detectable for PI3k and ARID1 after about two weeks of treatment (FIG. 17). After about two weeks of treatment, her CTCs showed resolution of telomerase activity compared to before therapy. After about one month of therapy, the CTCs were tested again and showed only marginally elevated ERBB2 (i.e., ERBB2 was only marginally above threshold (>2.0)) indicating that the CTC burden in the blood was likely very low/reduction in CTC burden in the blood. This result was obtained after 15 treatments.

She was restaged with a whole body PET scan and a significant response to the combination therapy was observed with reduced sizes or complete resolution of the lesions in the chest, abdomen, and pelvis. The retroperitoneal, para aortic LNs and bladder lesion and adrenal lesion had completely resolved. All left upper quadrant lesions had shrunk in size (largest from 3.0 cm to 1.6 cm) as well as liver surface (from 3.4 cm to 2.4 cm) and left kidney (from 3.0 cm down to 1.7 cm). Mesenteric node decreased from 2.4 cm to 1.3 cm.

The patient moved after about 10 months of starting treatment, and was not able to continue the epigenetic therapies as scheduled. She remained on PARP inhibitor (Niraparib at 300 mg daily).

About one month after moving, she was admitted to the hospital for an episode of abdominal distention and partial obstruction. She was restaged with abdominal CT scan. Her scan showed mixed response with progression specifically in her retroperitoneal (21 mm from 16 mm) and periaortic nodes (32 from 24 mm) as well as abdominal mesenteric artery LN (28 mm from 16 mm).

In summary, such an unusual response to the combinational therapy in a BRCA positive refractory stage four ovarian CA using epigenetic therapies in conjunction with a PARP inhibitor was unexpected, and could potentially translate to better outcome if adopted as the standard of care.

Example 6—Case Study 3

This is a case study of a 60-year-old male with history of stage four pancreatic cancer who was diagnosed after abdominal pain, with adenocarcinoma of pancreas metastasized to his liver. He had explored all potential therapies and his oncologist had given him less than 3 months to live and had referred him to hospice.

He arrived at the clinic of Dr. Nezami, and initial laboratory tests showed increased tumor markers CEA, CA 19.9 as well as angiogenesis markers, VEGF and IL-8. He was immediately started on daily IV epigenetic therapies in combination with PARP inhibitors, which he received for two weeks after which his laboratory tests were repeated.

Figure 19:
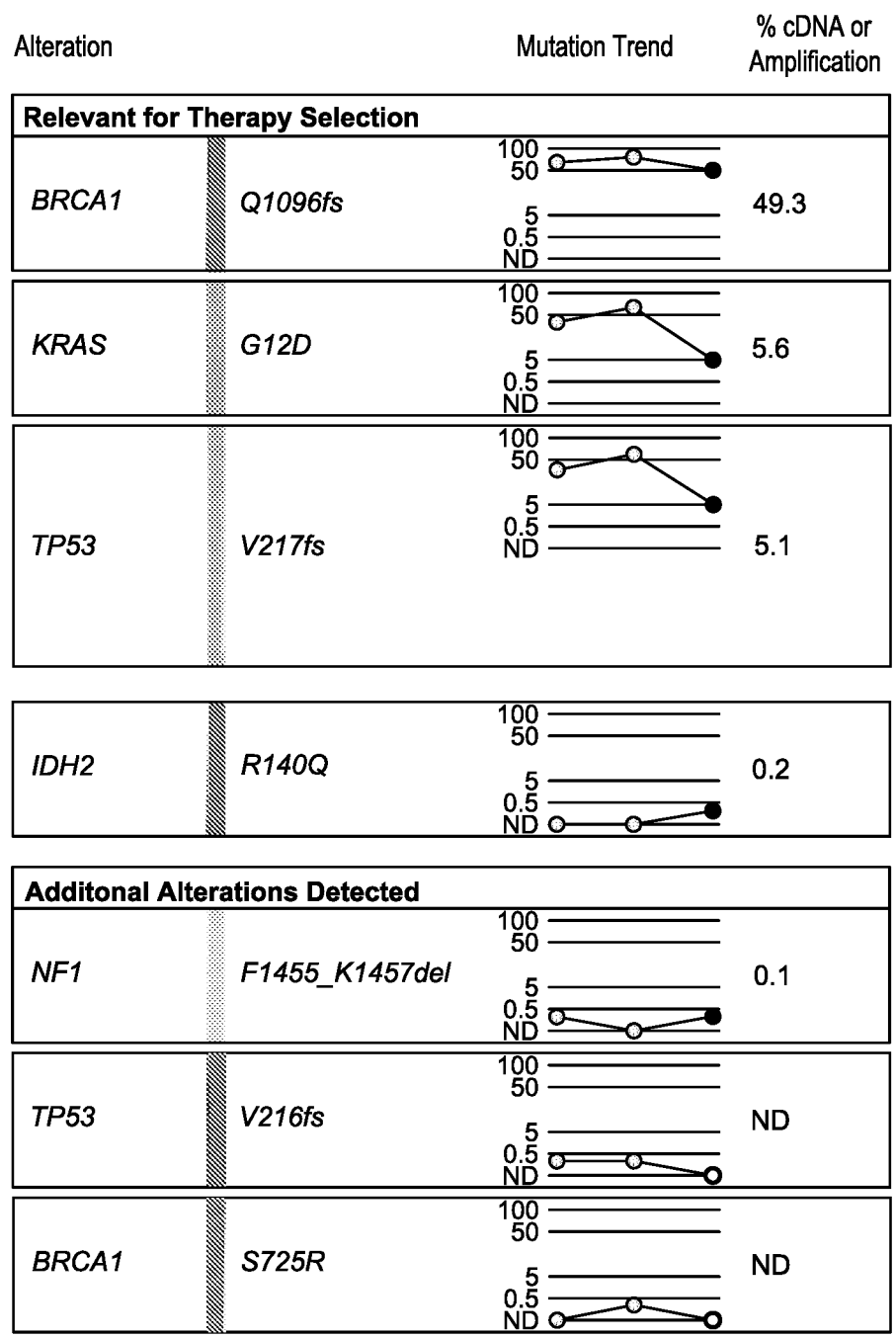
FIG. 19 shows a summary of somatic alterations from Example 6.
Figure 19:
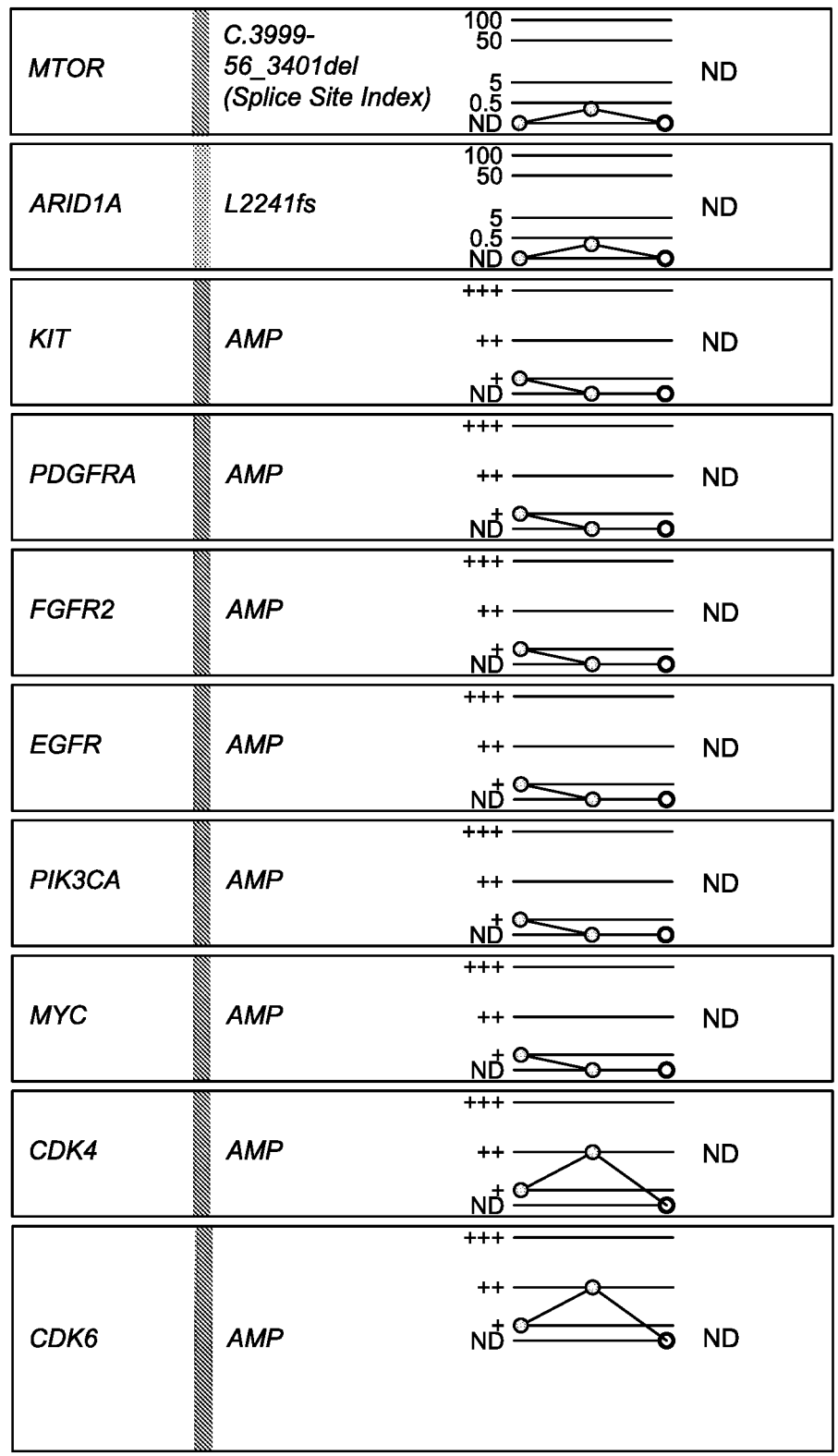

After two weeks of epigenetic therapies, his VEGF decreased from 248 to 70. His IL-8 also decreased from 114 to 106 (in plasma) and 99 to 48 (in serum). Additionally, his cDNA, showed significant alterations in following genes—FGF2, C Myc, EGFR, PI3K, CDK4, CDK6, NF-1, KIT, TP53, PDGF, KRAS, BRCA1 (FIG. 19). These alterations did not change with taking Lynparza alone. He did not receive any other modalities of care, and did not change his diet or did not take supplements with the epigenetic therapies in combination with PARP inhibitors.

With epigenetic therapies in combination with PARP inhibitors, his quality of life improved drastically and his pain medication requirement significantly decreased. He was able to walk again independently. He started to do clinically well. His pain completely stopped. Edema in his lower extremities improved. His appetite was significantly better.

His laboratory tests showed significant reduction in VEGF (decreased from 280 to 70 (normal) and IL-8 decreased from 280 to 48 with three weeks of therapy. His laboratory tests were repeated after about five months of therapy and results showed that TGF had decreased from 9317 to 3365 with two months of therapy.

Figure 18:
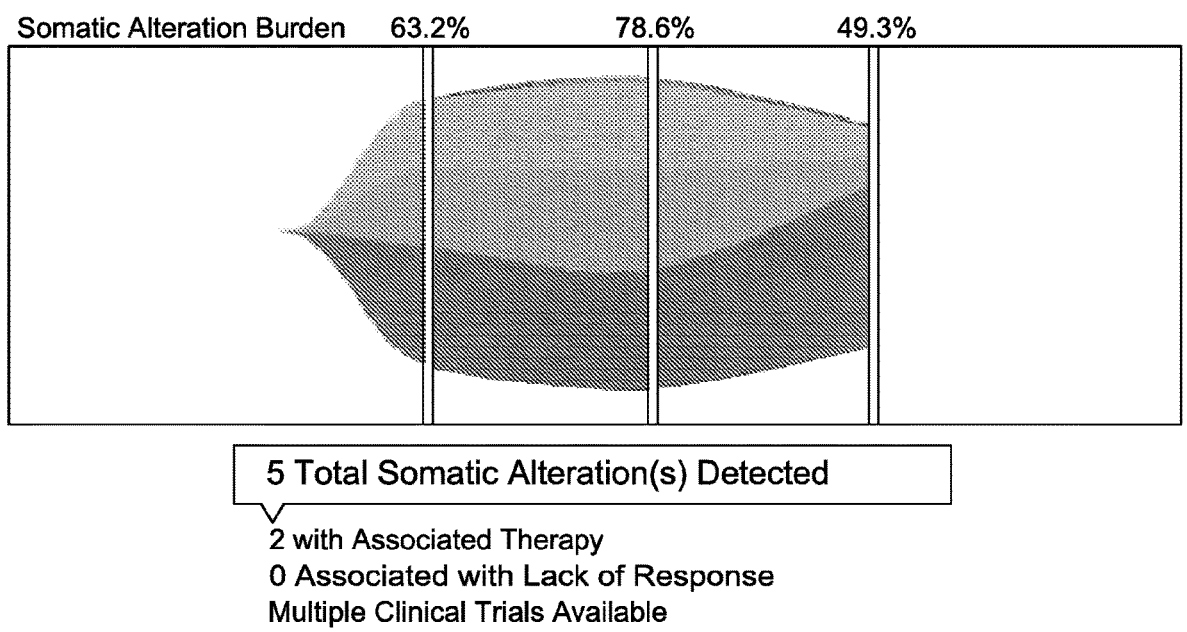
FIG. 18 shows an embodiment of a Guardant360 Tumor Response Map (see, Example 6).

After about five months of therapy, assay for % cfDNA with somatic alterations was repeated and results showed significant reduction in the presence of somatic alterations (FIG. 18). For example, KRAS mutant allele frequency (MAF) decreased from over 50 percent to 5.6, TP53 decreased from over 50 percent down to 5.1 percent (FIG. 19). Other alteration such as BRCA1, MTOR, ARID1, KIT, PDGF, FGFR2, PI3K, Myc, CDK4, CDK6 were not detectable and had resolved (FIG. 19).

When he stopped the epigenetic therapies, his disease progressed despite continuing his conventional therapy, Lynparza. Thus, Lynparza alone was not sufficient to retard tumor growth. Upon his return to the clinic, his tumor marker CA 19.9 was analyzed. Results showed that CA 19.9 had increased from 8565 to 45988 during the two months that he did not receive epigenetic therapies, which was twice the expected level of tumor growth with no epigenetic therapies.

In summary, the tumor growth was significantly reduced when epigenetic therapies were provided in conjunction with PARP inhibitors. The tumor showed significant reduction in heterogeneity as well as BRCA fingerprint as determined based on liquid biopsy.

The terminology used in the description presented herein is not intended to be interpreted in any limited or restrictive manner and unless otherwise indicated refers to the ordinary meaning as would be understood by one of ordinary skill in the art in view of the specification. Furthermore, embodiments may comprise, consist of, or consist essentially of, several novel features, no single one of which is solely responsible for its desirable attributes or is believed to be essential to practicing the embodiments herein described. As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

Although this disclosure is in the context of certain embodiments and examples, those of ordinary skill in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of ordinary skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

What is claimed is:

1. A method of treatment of a neoplasm, the method comprising:
    administering, to a patient in need thereof, synergistically effective amounts of:
        a PARP inhibitor; and
        a first anti-cancer response modulator, wherein the first anti-cancer response modulator is quercetin, and
    wherein the neoplasm is BRCA mutation positive.

2. The method of claim 1, wherein the PARP inhibitor is administered at a dose of about 0.0075 mg/kg to about 20 mg/kg.

3. The method of claim 1, wherein the first anti-cancer response modulator is quercetin, and is administered at a dose of 0.1 g to 2.5 g.

4. The method of claim 1, wherein the neoplasm is selected from the group consisting of a triple negative breast cancer wherein the triple negative breast cancer is estrogen receptor-negative, progesterone receptor-negative and human epidermal growth factor receptor 2 (HER2/NEU)-negative, and a breast cancer in an individual with germline BRCA1 mutation, germline BRCA2 mutation or both.

5. The method of claim 2, wherein the PARP inhibitor is selected from the group consisting of Olaparib, Veliparib, Niraparib, Talazoparib, Rucaparib, CEP-9722, and Iniparib.

6. The method of claim 5, wherein the PARP inhibitor is Olaparib and wherein the amount of Olaparib is about 100 mg to about 800 mg per day.

7. The method of claim 1, wherein the anti-cancer response modulator is in a nanoparticle formulation.

8. The method of claim 3, wherein the anti-cancer response modulator is in a nanoparticle formulation.

9. The method of claim 1, further comprising a second anti-cancer response modulator selected form the group consisting of SPB, EGCG, and combinations thereof.

10. The method of claim 7, further comprising a second anti-cancer response modulator selected form the group consisting of SPB, EGCG, and combinations thereof.

11. The method of claim 8, further comprising a second anti-cancer response modulator selected form the group consisting of SPB, EGCG, and combinations thereof.

* * * * *